United States Patent [19]
Coghlan et al.

[11] Patent Number: 6,166,013
[45] Date of Patent: Dec. 26, 2000

[54] GLUCOCORTIOCOID-SELECTIVE AGENTS

[75] Inventors: Michael J. Coghlan, Grayslake, Ill.; Jay R. Luly, Wellesley, Mass.; Jeffrey M. Schkeryantz, Fishers, Ind.; Alan X. Wang, Guilford, Conn.

[73] Assignee: Abbott Laboratories, Abbott Park, Ill.

[21] Appl. No.: 09/365,268

[22] Filed: Jul. 30, 1999

Related U.S. Application Data

[60] Provisional application No. 60/094,699, Jul. 30, 1998.

[51] Int. Cl.$^7$ ...................... A61K 31/535; A61K 31/135; C07D 413/04; C07D 211/26
[52] U.S. Cl. ...................... 514/239.5; 514/331; 514/408; 514/429; 514/646; 544/165; 546/229; 546/232; 546/235; 548/577; 560/535; 564/326; 252/104
[58] Field of Search .................. 252/104; 514/237.8, 514/239.5, 408, 429, 535, 331, 646; 560/575; 564/326; 544/165; 548/577; 546/229, 232, 235

[56] References Cited

U.S. PATENT DOCUMENTS

| 4,152,341 | 5/1979 | Jones et al. ............................. 260/395 |
| 5,112,867 | 5/1992 | Kinoshita et al. ...................... 514/617 |

FOREIGN PATENT DOCUMENTS

| 0153872 | 9/1985 | European Pat. Off. . |
| 0159870 | 10/1985 | European Pat. Off. . |
| 0395093 | 10/1990 | European Pat. Off. . |
| 2503309 | 8/1975 | Germany . |
| 59-036255 | 2/1984 | Japan . |
| 9734589 | 9/1997 | WIPO . |
| WO 9734589 | 9/1997 | WIPO . |
| 9932101 | 7/1999 | WIPO . |

OTHER PUBLICATIONS

A. Nieto, et al, Biochemistry International, 1990, vol. 21, No. 2, pp. 305–311, "In Vivo Estrogenic and Antiestrogenic Activity of Phenolphthalein and Derivative Compounds".

Nieto, et al., Biochemistry International, 1990, vol. 21, No. 2, 305–311.

Greene, T.W. & Wuts, P.G.M. (1991) Protective Groups in Organic Synthesis (2$^{nd}$ ed.) New York: John Wiley & Sons.

Edward B. Roche, Bioreversible Carries in Drug Design, American Pharmaceutical Association and Pergamon Press, 1987.

S. M. Berge, et al., J. Pharmaceutical Sciences, 1977, 66:1–19.

Anal. Biochem, 1970, 37, 244–252.

Summers, M.D., Smith, G.E., A Manual of Methods for Baculovirus Vectors and Insect Cell Culture Procedures, Tex. Agric. Exp. Stn. [Bull], 1987, No. 155.

Wecksler, W.R., Norman, A.W., An Hydroxylapatite Batch Assay for the Quantitation of 1a, 25–Dihydroxyvitamin D3–Receptor Complexes, Anal. Biochem. 1979, 92, 314–323.

Chen, Y., et al., Relationship Between the Inhibition Constant (Ki) and the Cnecentration of Inhibitor Which Causes 50% Inhibition (IC50) of an Enzymatic Reaction, Biochem. Pharmacol., 1973, 22, 3099–3108.

DeBlasi, A., et al., Calculating Receptor Number from Binding Experiments Using Same Compound as Radioligand and Competitor, TIPS 1989, 10, 227–229.

Pham, T.A., et al., Ligand–Dependent and Independent Function of the Transactivation Regions of the Human Estrogen Receptor in Yeast, Mol. Endocrinol. 1992, 6, 1043–1050.

Loose, D., Ketoconazole Binds to Glucocorticoid Receptors and Exhibits Glucocorticoid Antagonist Activity in Cultured Cells, Journal of Clinical Investigation, US, vol. 72, Jul. 1, 1983, pp. 404–408.

*Primary Examiner*—Joseph McKane
*Assistant Examiner*—Ebenezer Sackey
*Attorney, Agent, or Firm*—Lawrence S. Pope

[57] ABSTRACT

Compounds having Formula I

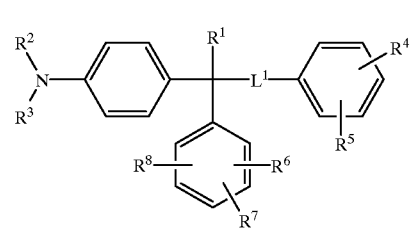

are useful for modulating the glucocorticoid receptor in a mammal. Also disclosed are pharmaceutical compositions comprising compounds of Formula I and methods of treating immune, autoimmune, inflammatory, adrenal imbalance, cognitive and behavioral diseases in a mammal.

9 Claims, No Drawings

GLUCOCORTIOCOID-SELECTIVE AGENTS

This application claims the benefit of U.S. Provisional application Ser. No. 60/094,699, filed Jul. 30, 1998.

TECHNICAL FIELD

The present invention relates to compounds which are selective for glucocorticoid receptors, pharmaceutical compositions comprising these compounds, and to methods of treating immune, autoimmune, inflammatory, adrenal imbalance, cognitive, and behavioral diseases.

BACKGROUND OF THE INVENTION

Intracellular receptors (IR's) are a class of structurally related proteins involved in the regulation of gene expression. The steroid hormone receptors are a subset of this superfamily whose natural ligands are typically comprised of endogenous steroids such as estradiol, progesterone, and cortisol. Man-made ligands to these receptors play an important role in human health and, of these receptors, the glucocorticoid receptor (GR) has an essential role in regulating human physiology and immune response. Steroids which interact with GR have been shown to be potent antiinflammatory agents. Despite this benefit, steroidal GR ligands are not selective. Side effects associated with chronic dosing are believed to be the result of cross-reactivity with other steroid receptors such as estrogen, progesterone, androgen, and mineralocorticoid receptors which have homologous ligand binding domains.

A ligand which is selective for GR over other IRs could modulate (i.e. repress, agonize, partially agonize, or antagonize) and thus can be used to influence the basic, life-sustaining systems of the body including carbohydrate, protein and lipid metabolism and the functions of the cardiovascular, kidney, central nervous, immune, skeletal muscle, and other organ and tissue systems. In this regard, GR modulators have proven useful in the treatment of inflammation, tissue rejection, auto-immunity, malignancies such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, and Little's syndrome.

GR modulators are especially useful in disease states involving systemic inflammation such as inflammatory bowel disease, systemic lupus erythematosus, polyartitis nodosa, Wegener's granulomatosis, giant cell arteritis, rheumatoid arthritis, osteoarthritis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, and cirrhosis. GR active compounds have also been used as immunostimulants, repressors, and wound healing and tissue repair agents.

GR modulators have also found use in a variety of topical diseases such as inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, herpes gestationis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitis, erythema nodosum, acne, hirsutism, toxic epidermal necrolysis, erythema multiform, and cutaneous T-cell lymphoma.

Selective antagonists of the glucocorticoid receptor have been unsuccessfully pursued for decades. These agents would potentially find application in several disease states associated with Human Immunodeficiency Virus (HIV), cell apoptosis, and cancer including, but not limited to, Kaposi's sarcoma, immune system activation and modulation, desensitization of inflammatory responses, IL-1 expression, antiretroviral therapy, natural killer cell development, lymphocytic leukemia, and treatment of retinitis pigmentosa. Cognitive and behavioral processes are also susceptible to glucocorticoid therapy where antagonists would potentially be useful in the treatment of processes such as cognitive performance, memory and learning enhancement, depression, addiction, mood disorders, chronic fatigue syndrome, schizophrenia, stroke, sleep disorders, and anxiety.

The prior art discloses a variety of triarylmethanes including triphenylmethanes useful as dyes or pigments. We have unexpectedly discovered a series of triphenylmethane compounds which selectively modulate the glucocorticoid receptor in relation to the progesterone receptor, minerocorticoid receptor, androgen receptor, and estrogen receptor-alpha. In addition, we provide a series of novel compounds which are selective for GR. Importantly, it has not been known previously that triphenylmethane compounds of this invention are useful as selective glucocorticoid receptor modulators.

Examples of the prior art include:

Aoyama et al. (European Patent application 85301391.0, published Sep. 04, 1985) discloses triarylmethane compounds which include triphenylmethane compounds that function as pigments during the process of determining the reduced form of nicotinamide adenine dinucleotide (phosphate);

Aoyama et al. (European Patent application 85302562.5, published Oct. 30, 1985) discloses triphenylmethane compounds that function as pigments during the process of determining compounds that contain a mercapto group;

Nieto et al. (Biochemistry International, 1990, Vol. 21, No. 2, 305–311) discloses that phenolphthalein, a dye containing a triphenylmethane structure, or a phenolphthalein derivative interacts with the rat estrogen receptor;

Kinoshita et al. (U.S. Pat. No. 5,112,867, issued May 12, 1992) discloses triphenylmethane compounds that are useful for treating osteoporosis; and Brugnara et al. (International Patent application 97/34589, published Sep. 25, 1997) discloses triphenylmethane compounds that have utility for inhibiting or treating sickle cell diseases and cell proliferation diseases in mammals.

SUMMARY OF THE INVENTION

In the principle embodiment of the present invention is disclosed a method of selectively modulating the glucocorticoid receptor in a mammal comprising administering an effective amount of a compound of Formula I

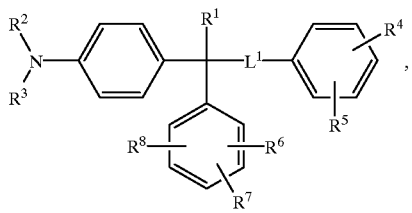

or a pharmaceutically acceptable salt or prodrug thereof, where
$R^1$ is selected from
  (1) hydrogen and
  (2) —OH;
$L^1$ is selected from
  (1) a covalent bond,
  (2) —O—,
  (3) —S(O)$_t$— where t is an integer from 0 to 2, and
  (4) —NR$^9$— where $R^9$ is selected from
    (a) hydrogen and
    (b) allyl of one to four carbons;
$R^2$ and $R^3$ are independently selected from
  (1) hydrogen,
  (2) an amino-protecting group,
  (3) alkyl of one to six carbons, and
  (4) alkyl of one to six carbons substituted with 1, 2, or 3 substituents independently selected from
    (a) phenyl and
    (b) —OR$^{10}$ where $R^{10}$ is selected from
      (i) hydrogen,
      (ii) alkyl of one to six carbons,
      (iii) a hydroxy-protecting group, and
      (iv) —C(O)R$^{11}$ where $R^{11}$ is selected from
        alkyl of one to six carbons,
        phenyl, and
        phenyl substituted with 1, 2, or 3 substituents selected from
          —NO$_2$,
          alkyl of one to six carbons, and
          halogen, or
$R^2$ and $R^3$ together with the nitrogen to which they are attached form a 4 to 8 membered ring selected from the group consisting of heterocycle;
$R^4$ and $R^5$ are independently selected from
  (1) hydrogen,
  (2) halogen,
  (3) —NR$^{12}$R$^{13}$ where $R^{12}$ and $R^{13}$ are independently selected from
    (a) hydrogen,
    (b) an amino-protecting group,
    (c) alkyl of one to six carbons, and
    (d) alkyl of one to six carbons substituted with 1, 2, or 3 substituents independently selected from
      (i) —OR$^{10}$ and
      (ii) phenyl, or
$R^{12}$ and $R^{13}$ together with the nitrogen to which they are attached form a 4 to 8 membered ring selected from the group consisting of heterocycle,
  (4) alkyl of one to six carbons, and
  (5) alkyl of one to six carbons substituted with 1, 2, or 3 substituents independently selected from
    (a) halogen,
    (b) —OR$^{10}$,
    (c) —CN, and
  (d) —CO$_2$R$^{14}$ where $R^{14}$ is selected from
    (i) hydrogen,
    (ii) alkyl of one to six carbons, and
    (iii) alkyl of one to six carbons substituted with 1, 2, or 3 substituents independently selected from
      phenyl and
      phenyl substituted with 1, 2, or 3 substituents independently selected from
        —NO$_2$,
        alkyl of one to six carbons, and
        halogen, and
  (e) —NR$^{15}$R$^{16}$ where $R^{15}$ and $R^{16}$ are independently selected from
    (i) hydrogen,
    (ii) an amino-protecting group,
    (iii) alkyl of one to six carbons, and
    (iv) alkyl of one to six carbons substituted with 1, 2, or 3 substituents independently selected from
      phenyl and
      phenyl substituted with 1, 2, or 3 substituents
        independently selected from
          —NO$_2$,
          alkyl of one to six carbons, and
          halogen;
$R^6$, $R_7$, and $R^8$ are independently selected from
  (1) hydrogen,
  (2) halogen,
  (3) alkyl of one to six carbons,
  (4) alkyl of one to six carbons substituted with 1, 2, or 3 substituents independently selected from
    (a) halogen,
    (b) —OR$^{10}$,
    (c) —CN,
    (d) —CO$_2$R$^{14}$ and
    (e) —NR$^{15}$R$^{16}$,
  (5) perfluoroalkyl of one to six carbons,
  (6) —NR$^{17}$R$^{18}$ where $R^{17}$ and $R^{18}$ are independently selected from
    (a) hydrogen,
    (b) an amino-protecting group,
    (c) alkyl of one to six carbons,
    (d) alkyl of one to six carbons substituted with 1, 2, or 3 substituents independently selected from
      (i) phenyl,
      (ii) heterocycle, and
      (iii) —OR$^{10}$,
    (e) —C(O)R$^{19}$ where $R^{19}$ is selected from
      (i) alkyl of one to six carbons,
      (ii) alkyl of one to six carbons substituted with 1, 2, or 3 substituents independently selected from
        heterocycle,
        phenyl, and
        phenyl substituted with 1, 2, or 3 substituents independently selected from
          alkyl of one to six carbons,
          halogen,
          —NO$_2$,
          —CF$_3$,
          —CN,
          —C(O)R$^{20}$ where $R^{20}$ is selected from
            hydrogen,
            alkyl of one to six carbons,
            —NR$^{21}$R$^{22}$ where $R^{21}$ and $R^{22}$ are independently selected from hydrogen,
an amino-protecting group, and
alkyl of one to six carbons, and
—$OR^{23}$ where $R^{23}$ is selected from alkyl of one to six carbons and alkyl of one to six carbons substituted with 1, 2, or 3 substituents independently selected from the group consisting of halogen,
(iii) cycloalkyl of three to six carbons,
(iv) cycloalkyl of three to six carbons substituted with 1, 2, or 3 substituents independently selected from
heterocycle,
phenyl,
phenyl substituted with 1, 2, or 3 substituents independently selected from
—$NO_2$,
alkyl of one to six carbons, and
halogen,
halogen,
—CN,
—$CO_2R^{14}$,
alkyl of one to six carbons, and
alkyl of one to six carbons substituted with 1, 2, or 3 substituents independently selected from the group consisting of halogen,
(v) alkenyl of two to six carbons,
(vi) alkenyl of two to six carbons substituted with 1 or 2 substituents independently selected from
heterocycle,
phenyl, and
phenyl substituted with 1, 2, or 3 substituents independently selected from
alkyl of one to six carbons,
halogen,
—$NO_2$,
—$CF_3$,
—CN, and
—$CO_2R^{14}$,
(vii) phenyl,
(viii) phenyl substituted with 1, 2, or 3 substituents independently selected from
halogen,
alkyl of one to six carbons,
—$NO_2$,
—$CF_3$,
—CN, and
—$CO_2R^{14}$, and
(ix) —$OR^{11}$, and
(f) —$SO_2R^{24}$ where $R^{24}$ is selected from
(i) alkyl of one to six carbons,
(ii) phenyl, and
(iii) phenyl substituted with 1, 2, or 3 substituents independently selected from
alkyl of one to six carbons and
—$NO_2$,
(7) —$OR^{25}$ where $R^{25}$ is selected from
(a) perfluoroalkyl of one to six carbons,
(b) alkyl of one to six carbons,
(c) alkyl of one to six carbons substituted with 1, 2, or 3 substituents independently selected from
(i) halogen and
(ii) phenyl,
(d) a hydroxy-protecting group, and
(e) —$C(O)R^{14}$,
(8) —CN,
(9) —$C(O)R^{19}$,
(10) —$CO_2R^{14}$,
(11) —$C(O)R^{20}$,
(12) —$SO_2NR^{26}R^{27}$ where $R^{26}$ and $R^{27}$ are independently selected from,
(a) alkyl of one to six carbons,
(b) phenyl, and
(c) phenyl substituted with 1, 2, or 3 substituents independently selected from
(i) alkyl of one to six carbons,
(ii) halogen, and
(iii) —$NO_2$,
(13) —$S(O)_tR^{28}$ where t is defined previously and $R^{28}$ is selected from
(a) hydrogen,
(b) perfluoroalkyl of one to six carbons,
(c) alkyl of one to six carbons,
(d) alkyl of one to six carbons substituted with 1, 2, or 3 substituents independently selected from
(i) phenyl and
(ii) phenyl substituted with 1, 2, or 3 substituents independently selected from
alkyl of one to six carbons,
halogen, and
—$NO_2$,
(e) phenyl, and
(f) phenyl substituted with 1, 2, or 3 substituents independently selected from
(i) alkyl of one to six carbons,
(ii) halogen, and
(iii) —$NO_2$,
(14) —$NO_2$,
(15) —$N=CHR^{29}$ where $R^{29}$ is selected from
(a) phenyl,
(b) aryl, and
(c) heterocycle, and
(16)

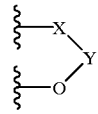

where X is selected from —$CH_2$—, —$CH_2O$— and —O—, and Y is selected from —C(O)— and —$(C(R")_2)_v$—, where R" is hydrogen or alkyl of one to four carbons, and v is an integer from 1 to 3.

In still another embodiment of the present invention is disclosed a method of treating inflammation and immune, autoimmune and inflammatory diseases in a mammal comprising administering an effective amount of a compound of Formula I.

In still another embodiment of the present invention is disclosed a method of treating adrenal imbalance in a mammal comprising administering an effective amount of a compound of Formula I.

In still another embodiment of the present invention is disclosed a method of treating cognitive and behavioral processess susceptible to glucocorticoid therapy where antagonists would be useful in the treatment of processes such as cognitive performance, memory and learning enhancement, depression, addiction, mood disorders, chronic fatigue syndrome, schizophrenia, stroke, sleep disorders, and anxiety in a mammal comprising administering an effective amount of a compound of Formula I.

In still another embodiment of the present invention is disclosed pharmaceutical compositions containing compounds of Formula I.

Compounds of this invention include, but are not limited to,

4',4"bis(dimethylamino)-2-chloro-5-nitrotriphenylmethane,
4',4"bis(dimethylamino)-4-chloro-3-nitrotriphenylmethane,
4',4"bis(dimethylamino)-5-acetamido-2-chlorotriphenylmethane,
4',4"bis(dimethylamino)-4-nitrotriphenylmethane,
4',4"bis(dimethylamino)-4-chlorotriphenylmethane,
4',4"bis(dimethylamino)-3-chlorotriphenylmethane,
4',4"bis(dimethylamino)-2-chlorotriphenylmethane,
4',4"bis(dimethylamino)-2-methoxytriphenylmethane,
4',4"bis(dimethylamino)-3-nitrotriphenylmethane,
4',4"bis(dimethylamino)-2-trifluoromethyltriphenylmethane,
4',4"bis(dimethylamino)triphenylmethane,
4',4"bis(dimethylamino)-2-chloro-6-nitrotriphenylmethane,
4',4"bis(N-piperidinyl)-2-chloro-5-nitrotriphenylmethane,
4',4"bis(dimethylamino)-2-bromotriphenylmethane,
4',4"bis(dimethylamino)-2-methyltriphenylmethane,
4',4"bis(dimethylamino)-2,3,5-trichlorotriphenylmethane,
4',4"bis(dimethylamino)-2-chloro-5-trifluoromethyltriphenylmethane,
4',4"bis(dimethylamino)-2,4-dichlorotriphenylmethane,
4',4"bis(dimethylamino)-2-chloro-4,5-methylenedioxytriphenylmethane,
4',4"bis(dimethylamino)-2,6-dichlorotriphenylmethane,
4',4"bis(dimethylamino)-2,3-dichlorotriphenylmethane,
4',4"bis(N-morpholinyl)-2-chloro-5-nitrotriphenylmethane,
4',4"bis(methylamino)-2-chloro-5-nitrotriphenylmethane,
4',4"bis(dimethylamino)-2,5-dichlorotriphenylmethane,
4',4"bis(dimethylamino)-2-fluorotriphenylmethane,
4',4"bis(dimethylamino)-2-iodotriphenylmethane,
4',4"bis(methylamino)-2,5-dichlorotriphenylmethane,
4',4"bis(N-morpholinyl)-2,3,5-trichlorotriphenylmethane,
4',4"bis(N-pyrrolidinyl)-2-chloro-5-nitrotriphenylmethane,
4',4"bis(di-n-butylamino)-2-chloro-5-nitrotriphenylmethane,
4',4"bis(N-(2-acetoxyethyl) N-methylamino)-2-chloro-5-nitrotriphenylmethane,
4',4"bis(N-(2-hydroxyethyl) N-methylamino)-2-chloro-5-nitrotriphenylmethane,
4',4"bis(dimethylamino)-2-chloro-5-iodotriphenylmethane,
4',4"bis(dimethylamino)-5-bromo-2-chlorotriphenylmethane,
4',4"bis(N-(t-butoxycarbonyl) N-methylamino)-2-chloro-5-nitrotriphenylmethane,
4',4"bis(N-benzylamino)-2-chloro-5-nitrotriphenylmethane,
4',4"bis(N-benzylamino)-2,5-dichlorotriphenylmethane,
4',4"bis(dimethylamino)-4-methoxytriphenylmethane,
4'-dimethylamino-4"-methylamino-2-chloro-5-nitrotriphenylmethane,
4'-dimethylamino-4"-(N-morpholinyl)-2-chloro-5-nitrotriphenylmethane,
4'-dimethylamino-4"-(N-pyrrolidinyl)-2-chloro-5-nitrotriphenylmethane,
4'-dimethylamino-4"-(N-methyl-N-(2-hydroxyethyl)amino)-2-chloro-5-nitrotriphenylmethane,
4'-dimethylamino-4"-(di-n-butylamino)-2-chloro-5-nitrotriphenylmethane,
3'-methyl-4',4"-bis(dimethylamino)-2-chloro-5-nitrotriphenylmethane,
4'-dimethylamino-4"-(N-piperidinyl)-2-chloro-5-nitrotriphenylmethane,
4'-methylamino-4"-(t-butoxycarbonylamino)-2-chloro-5-nitrotriphenylmethane,
4'-methylamino-4"-(N-(2-acetoxyethyl)-N-methylamino)-2-chloro-5-nitrotriphenylmethane,
4'-dimethylamino-4"-(N-methyl-N-(2-benzoyloxyethyl)amino)-2-chloro-5-nitrotriphenylmethane,
4'-dimethylamino-4"-(N-methyl-N-(2-acetoxyethyl)amino)-2-chloro-5-nitrotriphenylmethane,
phenyl-[(4'-dimethylaminophenyl)-(2-chloro-5-nitrophenyl)methyl] ether,
4-chlorophenyl-[(4'-dimethylaminophenyl)-(2-chloro-5-nitrophenyl)methyl] ether,
phenyl-[(4'-dimethylaminophenyl)-(2-chloro-5-nitrophenyl)methyl] thioether,
phenyl- [(4'-dimethylaminophenyl)-(2-chloro-5-nitrophenyl)methyl] amine,
4-dimethylamino-2-chloro-5-nitrotriphenylmethane,
4'-dimethylamino-2-chlorotriphenylmethanol,
4'-dimethylamino-2-chlorotriphenylmethane,
4',4"bis(dimethylamino)-5-amino-2-chlorotriphenylmethane,
4',4"bis(dimethylamino)-2-chloro-5-(4-nitrobenzamido)triphenylmethane,
4',4"bis(dimethylamino)-2-chloro-5-(4-nitrocinnamido)triphenylmethane,
4',4"bis(dimethylamino)-2-chloro-5-(cyclopropylcarbamido)triphenylmethane,
4',4"bis(dimethylamino)-2-chloro-5-(dimethylsulphonimido)triphenylmethane,
4',4"bis(dimethylamino)-2-chloro-5-(methoxycarbonylamino)triphenylmethane,
4',4"bis(dimethylamino)-2-chloro-5-(2-furanylmethylamino)triphenylmethane, and
4',4"bis(dimethylamino)-2-chloro-5-(2-furanylmethylamino)triphenylmethane.

DETAILED DESCRIPTION OF THE INVENTION

Definition of Terms

The term "alkenyl of two to six carbons" refers to a straight or branched chain hydrocarbon radical containing from two-to-six carbon atoms and also containing at least one carbon-carbon double bond. Representative examples of "alkenyl of two to six carbons" include but are not limited to groups such as ethenyl, propenyl, isobutenyl, 1-butenyl, 1,3-butadienyl, 2-pentenyl, 2-hexenyl, 1,5-hexadienyl and the like.

The term "alkyl of one to four carbons" refers to a straight or branched chain hydrocarbon radical containing from one-to-four carbon atoms. Representative examples of "alkyl of one to four carbons" include but are not limited to groups such as methyl, ethyl, n-propyl, iso-propyl, n-butyl, sec-butyl, iso-butyl, tert-butyl and the like. The term "alkyl of one to six carbons" refers to a straight or branched chain hydrocarbon radical containing from one-to-six carbon atoms. Representative examples of "alkyl of one to six carbons" include but are not limited to groups such as all of the previous examples as well as n-pentyl, isopentyl, neopentyl, n-hexyl and the like.

The term "amino" refers to —NH$_2$.

The term "amino-protecting group" refers to groups intended to protect an amino group against undersirable reactions during synthetic procedures. Commonly used N-protecting groups are disclosed in Greene, T. W., & Wuts, P. G. M. (1991). *Protectective Groups In Organic Synthesis* (2nd ed.). New York: John Wiley & Sons. Preferred N-protecting groups are formyl, acetyl, benzoyl, pivaloyl, t-butylacetyl, phenylsulfonyl, benzyl, t-butyloxycarbonyl (Boc), and benzyloxycarbonyl (Cbz).

The term "aryl" as used herein refers to a carbocyclic ring system having 6-10 ring atoms and one or two aromatic rings. Representative examples of aryl groups include groups such as, for example, phenyl, naphthyl, tetrahydronaphthyl, indanyl, indenyl and the like. The aryl groups of this invention can be optionally substituted.

The term "cycloalkyl of three to six carbons" refers to a saturated cyclic hydrocarbon radical containing from three-to-six carbon atoms. Representative examples of "cycloalkyl of three to six carbons" include but are not limited to groups such as, for example, cyclopropyl, cyclobutyl, cyclopentyl, cyclohexyl, and the like.

The term "halogen" refers to F, Cl, Br, or I.

The term "heterocycle" represents a represents a 4-, 5-, 6-, 7-, or 8-membered ring containing one, two or three heteroatoms independently selected from the group consisting of nitrogen, oxygen and sulfur. The 4- and 5-membered rings have zero to two double bonds, the 6- and 7-membered rings have zero to three double bonds and the 8-membered rings have zero to four double bonds. The term "heterocycle" also includes bicyclic, tricyclic and tetracyclic groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring. Heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolinyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, thiomorpholinyl, triazolyl, and the like.

Heterocyclics also include bridged bicyclic groups where a monocyclic heterocyclic group is bridged by an alkylene group such as

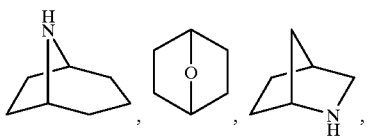

and the like.

Heterocyclics also include compounds of the formula

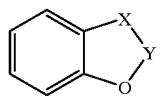

where X is selected from —CH$_2$—, —CH$_2$O— and —O—, and Y is selected from —C(O)— and —(C(R")$_2$)$_v$—, where R" is hydrogen or alkyl of one to four carbons, and v is 1–3. These heterocycles include 1,3-benzodioxolyl, 1,4-benzodioxanyl, and the like.

The term "hydroxy-protecting group" refers to a substituent which protects hydroxyl groups against undesirable reactions during synthetic procedures. Examples of hydroxy-protecting groups include, but are not limited to, ethers, for example, methyl, ethyl, t-butyl, benzyl and allyl; substituted methyl ethers, for example, methoxymethyl, benzyloxymethyl, 2-methoxyethoxymethyl, 2-(trimethylsilyl)-ethoxymethyl, and triphenylmethyl; substituted ethyl ethers, for example, 2,2,2-trichloroethyl and t-butyl; tetrahydropyranyl ethers; silyl ethers, for example, trimethylsilyl, t-butyldimethylsilyl and t-butyldiphenylsilyl; esters, for example, formate, acetate, trifluoroacetate, pivalate, benzoate, and adamantoate; carbonates, for example, methyl, ethyl, isobutyl, t-butyl, vinyl, allyl, and benzyl; sulfonates, for example, methanesulfonate, benzylsulfonate and p-toluenesulfonate. Commonly used hydroxy-protecting groups are disclosed in Greene, T. W., & Wuts, P. G. M. (1991). *Protectective Groups In Organic Synthesis* (2nd ed.). New York: John Wiley & Sons.

The term "Lewis acid" refers to any chemical species which has a vacant orbital and therefore acts as an electron pair acceptor. Representative examples of a "Lewis acid" include but are not limited to boron trifluoride, aluminum trichloride, titanium tetrachloride, and stannic tetrachloride.

The term "perfluoroalkyl of one to six carbons" refers to an alkyl group containing one-to-six carbon atoms where all the hydrogens have been substituted with fluorides.

The term "pharmaceutically acceptable prodrugs" represents those prodrugs of the compounds of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug" represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "pharmaceutically acceptable salt" represents those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences,* 1977, 66:1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Compounds of the present invention can exist as stereoisomers where asymmetric or chiral centers are present. These compounds are designated by the symbols "R" or "S" depending on the configuration of substitiuents around the chiral carbon atom. The present invention contemplates various stereoisomers and mixtures thereof. Stereoisomers include enantiomers and diastereomers, and equal mixtures of enantiomers are designated (±). Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of enantiomers on chiral chromatographic columns.

Determination of Biological Activity

For glucocorticoid receptor (GR) cytosol binding assays, the procedure described in Anal. Biochem. 1970, 37, 244–252, hereby incorporated by reference, was used. Briefly, cytosol preparations of human glucocorticoid receptor-α [GRX] isoform and human progesterone receptor-A [PRA] isoform were obtained from Ligand Pharmaceuticals (San Diego, Calif.). Both receptor cDNAs were cloned into baculovirus expression vectors and expressed in insect SF21 cells. [$^3$H]-dexamethasone (Dex, specific activity 82–86 Ci/mmole) and [$^3$H]-progesterone (Prog, specific activity 97–102 Ci/mmol) were purchased from Amersham Life Sciences (Arlington Heights, Ill.). Glass fiber type C multiscreen MAFC NOB plates were from Millipore (Burlington, Mass.). Hydroxyapatide Bio-Gel HTP gel was obtained from Bio-Rad Laboratories (Hercules, Calif.). Tris (hydroxymethyl)aminomethane (Tris), ethylenediaminetetraacetic acid (EDTA), glycerol, dithiothreitol (DTT) and sodium moylybdate were obtained from Sigma Chemicals (St. Louis, Mo.). Microscint-20 scintillation fluid was obtained from Packard Instrument (Meriden, Conn.).

Stock solutions (32 mM) of compounds were prepared in dimethylsulfoxide (DMSO), and 50× solutions of test compounds were prepared from the 32 mM solution with a 50:50 mixture of DMSO/ethanol. The 50× solution was then diluted with binding buffer that contained 10 mM Tri-HCl, 1.5 mM EDTA, 10% glycerol, 1 mM DTT, 20 mM sodium molybdate, pH 7.5 at 4° C. 1 % DMSO/ethanol was also present in the binding assay.

GRX and PRA binding reactions were performed in Millipore Multiscreen plates. For GR binding assays, [$^3$H]-Dex (~35,000 dpm (~0.9 nM)), GRX cytosol (~35 pg protein), test compounds and, binding buffer were mixed in a total volume of 200 μL and incubated at 4° C. overnight in a plate shaker. Specific binding was defined as the difference between binding of [$^3$H]Dex in the absence and in the presence of 1μM unlabeled Dex.

For progesterone receptor cytosol (PR) binding assays, [$^3$H]Prog (~36,000 dpm (~0.8 nM)), PRA cytosol (~40 μg protein), test compounds and binding buffer were mixed in a total volume of 200 μL and incubated at 4° C. overnight in a plate shaker. Specific binding was defined as the difference between binding of [3H]Prog in the absence and in the presence of 3 μM unlabeled Prog.

After an overnight incubation, 50 μL of hydroxyapatite (25% weight/volume) slurry were added to each well and plates were incubated for 10 min at 4° C. in a plate shaker. Plates were suctioned with a Millipore vacuum manifold and each well was rinsed with 300 μL of ice-cold binding buffer. A 250 μL aliquot of Packard Microscint-20 was added to each well and the wells were shaken at room temperature for 20 minutes. The amount of radioactivity was determined with a Packard TopCount plate reader.

For the determination of GR and PR inhibition constants ($K_i$), the concentration of test compounds that inhibited 50% of specific binding ($IC_{50}$) was determined from a Hill analysis of the competitive binding experiments. The $K_i$ of test compounds was determined using the Cheng-Prusoff equation $K_i = IC_{50}/(1+[L^*]/[K_L])$ where L* is the concentration of radioligand and $K_L$ is the dissociation constant of the radioligand determined from saturation analysis. For GRX, $K_L$ was ~1.5 nM, and for PRA, KL was ~4.5 nM.

For soluble minerocorticoid receptor (MR) binding assays, [$^3$H]-aldosterone (75–85 Ci/mmol) was purchased from New England Nuclear (Boston, Mass.), aldosterone was purchased from Sigma Chemical Co. (St. Louis, Mo.), CHAPS and DTf were purchased from Boehringer Mannheim GmbH (W. Germany) and all other reagents were purchased from Sigma.

The full length human androgen receptor was derived from cDNA expressed in a baculovirus expression system. The methods concerning growth, purification, and assays of recombinant viruses followed the protocol outlined by Summers, M. D., Smith, G. E., A Manual of Methods for Baculovirus Vectors and Insect Cell Culture Procedures, Tex. Agric. Exp. Stn. [Bull], 1987, No. 155, hereby incorporated by reference. The recombinant plasmids were cotransfected into SF21 cells with wild type AcNPV DNA, and the recombinant viruses were plaque purified.

A receptor extract was prepared from the baculovirus system, and aliquots were stored at −80° C. until used. Typical protein concentrations for these extracts were between 10 and 20 mg/ml. Stock solutions of aldosterone or other competing compounds were prepared as either 5 mM ethanol or DMSO stock solutions and serial dilutions were carried out in 1:1 DMSO-ethanol. The assay buffer consisted of the following: 25 mM sodium phosphate, 10 mM potassium fluoride, 20 mM sodium molybdate, 10% glycerol, 2 mM DTT and 0.25 mM CHAPS, pH=7.3 at room temperature.

Receptor assays were performed with a final volume of 250 μL containing from 50–75 μg of extract protein, plus 3–4 nM [$^3$H]-aldosterone and varying concentrations of competing ligand (0 to 10,000 nM). Assays were set up using a 96-well minitube system and incubations were carried out at 4° C. for 18 hours. Equilibrium under these conditions of buffer and temperature was achieved by 6–8 hours. Nonspecific binding was defined as that binding remaining in the presence of 1000 μM unlabeled aldosterone. At the end of the incubation period, 200 μL of 6.25% hydroxyapatite was added in wash buffer (binding buffer in the absence of DTT and CHAPS). Specific ligand binding to receptor was determined by a hydroxyapatite-binding assay according to the protocol outlined by Wecksler, W. R., Norman, A. W., An Hydroxylapatite Batch Assay for the Quantitation of 1α, 25-Dihydroxyvitamin $D_3$-Receptor Complexes, Anal. Biochem. 1979, 92, 314–323, hereby incorporated by reference. Hydroxyapatite absorbs the receptor-ligand complex, allowing for the separation of bound from free radiolabeled ligand. The mixture was vortexed, incubated for 10 minutes at 4° C., centrifuged, and the supernatant was removed. The hydroxyapatite pellet was washed twice more with the wash buffer. The amount of receptor-ligand complex was determined by liquid scintillation counting of the hydroxyapatite pellet after the addition of 0.5 mM EcoScint A scintillation cocktail from National Diagnostics (Atlanta, Ga.).

After correcting for nonspecific binding, $IC_{50}$ values were determined. The $IC_{50}$ value is defined as the concentration of competing ligand required to decrease specific binding by 50%. The $IC_{50}$ values were determined graphically from a log-logit plot of the data. $K_i$ values for the analogs were calculated by application of the Cheng-Prussof equation outlined by Cheng, Y.-C., Prusoff, W. F., Relationship Between the Inhibition Constant ($K_i$) and the Concentration of Inhibitor Which Causes 50% Inhibition ($IC_{50}$) of an Enzymatic Reaction, Biochem. Pharmacol. 1973, 22, 3099–3108, hereby incorporated by reference. Standards are included in each assay and resulting $K_i$ values are determined by use of a modified Cheng-Prusoff equation and used to calculate $K_i$ values for "unknown analogs" as outlined by DeBlasi, A., O'Reilly, K., Motulsky, H. J., Calculating Receptor Number from Binding Experiments Using Same Compound As Radioligand and Competitor, TIPS 1989, 10, 227–229, hereby incorporated by reference.

For human androgen receptor (AR) cytosol binding assays, [$^3$H]-dihydrotestosterone (DHT) (120–140 Ci/mmol) was purchased from Amersham Life Science (Arlington Heights, Ill.), DHT was purchased from Sigma Chemical Co. (St. Louis, Mo.), CHAPS and DTT were purchased from Boehringer Mannheim GmbH (W. Germany), and all other reagents were purchased from Sigma. The full length human androgen receptor (AR) was derived from cDNA expressed in a baculovirus expression system from Ligand Pharmaceuticals (San Diego, Calif.). The methods concerning growth, purification, and assays of recombinant viruses followed the protocol outlined by Summers, M. D., Smith, G. E., A Manual of Methods for Baculovirus Vectors and Insect Cell Culture Procedures, Tex. Agric. Exp. Stn. [Bull], 1987, No. 155, hereby incorporated by reference. The recombinant plasmids were cotransfected into SF21 cells with wild type AcNPV DNA, and the recombinant viruses were plaque purified.

A receptor extract was prepared from the baculovirus system, and aliquots were stored at −80° C. until used. Typical protein concentrations for these extracts were between 10 and 20 mg/ml. Stock solutions of DHT or other competing compounds were prepared as 5 mM stock solutions in either 100% ethanol or DMSO and serial dilutions were carried out in 1:1 DMSO-ethanol. The assay buffer consisted of the following: 25 mM sodium phosphate, 10 mM potassium fluoride, 10 mM sodium molybdate, 10% glycerol, 1.5 mM EDTA, 2 mM DTT, 2 mM CHAPS and 1 mM PMSF, pH=7.4 at room temperature.

Receptor assays were performed with a final volume of 250 μL containing from 50–75 μg of extract protein, plus 1–2 nM [$^3$H]-DHT and varying concentrations of competing ligand (0–10−5 M). Assays were set up using a 96-well minitube system and incubations were carried out at 4° C. for 18 hours. Equilibrium under these conditions of buffer and temperature was achieved by 6–8 hours. Nonspecific binding was defined as that binding remaining in the presence of 1000 nM unlabeled DHT. At the end of the incubation period, 200 μL of 6.25% hydroxyapatite was added in wash buffer (binding buffer in the absence of DTT and PMSF). Specific ligand binding to receptor was determined by a hydroxyapatite-binding assay according to the protocol outlined by Wecksler, W. R., Norman, A. W., An Hydroxylapatite Batch Assay for the Quantitation of 1α, 25-Dihydroxyvitamin $D_3$-Receptor Complexes, Anal. Biochem. 1979, 92, 314–323, hereby incorporated by reference. Hydroxyapatite absorbs the receptor-ligand complex, allowing for the separation of bound from free radiolabeled ligand. The mixture was vortexed, incubated for 10 minutes at 4° C., centrifuged, and the supernatant was removed. The hydroxyapatite pellet was washed twice more with the wash buffer. The amount of receptor-ligand complex was determined by liquid scintillation counting of the hydroxyapatite pellet after the addition of 0.5 mM EcoScint A scintillation cocktail from National Diagnostics (Atlanta, Ga.).

After correcting for nonspecific binding, $IC_{50}$ values were determined. The $IC_{50}$ value is defined as the concentration of competing ligand required to decrease specific binding by 50%. The $IC_{50}$ values were determined graphically from a log-logit plot of the data. $K_i$ values for the analogs were calculated by application of the Cheng-Prussof equation outlined by Cheng, Y.-C., Prusoff, W. F., Relationship Between the Inhibition Constant ($K_i$) and the Concentration of Inhibitor Which Causes 50% Inhibition ($IC_{50}$) of an Enzymatic Reaction, Biochem. Pharmacol. 1973, 22, 3099–3108, hereby incorporated by reference. Standards are included in each assay and resulting $K_i$ values are determined by use of a modified Cheng-Prusoff equation and used to calculate $K_i$ values for "unknown analogs" outlined by DeBlasi, A., O'Reilly, K., Motulsky, H. J., Calculating Receptor Number from Binding Experiments Using Same Compound As Radioligand and Competitor, TIPS 1989, 10, 227–229, hereby incorporated by reference.

For soluble estrogen receptor-alpha (ER-α) binding assays, [$^3$H]- Estradiol (120–140 Ci/mmol) was purchased from New England Nuclear (Boston, Mass.), 17-beta estradiol was purchased from Sigma Chemical Co. (St. Louis, Mo.), CHAPS and DTT were purchased from Boehringer Mannheim GmbH (W. Germany) and all other reagents were purchased from Sigma.

The human estrogen receptor-alpha cDNA was cloned into a yeast vector termed pYhERα and used to transform wild type yeast strain BJ2168 following the protocol outlined by Pham, T. A., Hwung Y. P., Santiso-Mere, D., McDonnell D. P., O'Malley, B. W., Ligand-Dependent and Independent Function of the Transactivation Regions of the Human Estrogen Receptor in Yeast, Mol. Endocrinol. 1992, 6, 1043–1050, hereby incorporated by reference. The yeast was induced with copper for 16 hours after which the cells were harvested, washed and the receptor extract prepared in cold buffer via a Bead Beater (BioSpec Products, Bartlesville, Okla.). Aliquots of the receptor typically contained 5–10 mg/ml of total protein and were stored at −80° C. until used. Estradiol or other competing compounds were prepared as 5 mM stock solutions in either 100% ethanol or DMSO and serial dilutions were carried out in 1:1 DMSO-ethanol. The assay buffer consisted of the following: 300 mM potassium chloride, 10 mM Trizma Base, 2 mM DTT and 5 mM CHAPS, pH=7.5 at room temperature.

Receptor assays were performed in a 250 μL final volume containing from 5–10 μg of extract protein, plus 2–3 nM [$^3$H]-estradiol and varying concentrations of competing ligand (0 to 10,000 nM). Assays were set up using a 96-well minitube system and incubations were carried out at 4° C. for 18 hours. Equilibrium under these conditions of buffer and temperature was achieved by 6–8 hours. Nonspecific binding was defined as that binding remaining in the presence of 1000 nM unlabeled estradiol. At the end of the incubation period, 200 μL of 6.25% hydroxyapatite was added in wash buffer (binding buffer in the absence of DTT but containing 1 mM CHAPS). Specific ligand binding to receptor was determined by a hydroxyapatite-binding assay according to the protocol outlined by Wecksler, W. R., Norman, A. W, An Hydroxylapatite Batch Assay for the Quantitation of 1α, 25-Dihydroxyvitamin $D_3$-Receptor Complexes, Anal. Biochem. 1979, 92, 314–323, hereby incorporated by reference. Hydroxyapatite absorbs the receptor-ligand complex, allowing for the separation of bound from free radiolabeled ligand. The mixture was vortexed, incubated for 10 minutes at 4° C., centrifuged, and the supernatant was removed. The hydroxyapatite pellet was washed twice more with the wash buffer. The amount of receptor-ligand complex was determined by liquid scintillation counting of the hydroxyapatite pellet after the addition of 0.5 mM EcoScint A scintillation cocktail from National Diagnostics (Atlanta, Ga.).

After correcting for nonspecific binding, $IC_{50}$ values were determined. The $IC_{50}$ value is defined as the concentration of competing ligand required to decrease specific binding by 50%. The $IC_{50}$ values were determined graphically from a log-logit plot of the data. $K_i$ values for the analogs were calculated by application of the Cheng-Prussof equation, Cheng, Y.-C., Prusoff, W. F., Relationship Between the Inhibition Constant ($K_i$) and the Concentration of Inhibitor Which Causes 50% Inhibition ($IC_{50}$) of an Enzymatic Reaction., Biochem. Pharmacol. 1973, 22, 3099–3108, hereby incorporated by reference. Standards are included in each assay and resulting $K_i$ values are determined by use of a modified Cheng-Prusoff equation and used to calculate $K_i$ values for "unknown analogs", DeBlasi, A., O'Reilly, K., Motulsky, H. J., Calculating Receptor Number from Binding Experiments Using Same Compound As Radioligand and Competitor, TIPS 1989, 10, 227–229, hereby incorporated by reference.

The $K_i$ of test compounds for MR, AR, and ER-α were determined using the Cheng-Prusoff equation, $K_{i\ analog} = IC_{50\ analog}/(1+[L]/K_{d(L)})$ where [L] is the labeled ligand on, $K_{d(L)}$ is the $K_d$ of the labeled ligand, and $IC_{50}$ is the concentration of analog to % of labeled ligand (determined graphically by log-logit plot of binding curve). inhibitory potencies of compounds of this invention and their selectivity for GR, ,and ER-α receptors are shown in Table 1.

TABLE 1

| Example Number | Ki (nM) | | | | |
|---|---|---|---|---|---|
| | GR | PR | MR | AR | ER-α |
| 1 | 272 | >10,000 | 2899 | 3731 | — |
| 2 | 4200 | — | — | — | — |
| 3 | 5154 | — | — | — | — |
| 4 | 4649 | — | — | — | — |
| 5 | 4649 | — | — | — | — |
| 6 | 2525 | — | — | — | — |
| 7 | 1992 | — | — | — | — |
| 8 | 4288 | — | — | — | — |
| 9 | 1385 | — | — | — | — |
| 10 | 2228 | — | — | — | — |
| 11 | 4649 | — | — | — | — |
| 12 | 3852 | — | — | — | — |
| 13 | 5002 | — | — | — | — |
| 14 | 1514 | — | — | — | — |
| 15 | 2961 | — | — | — | — |
| 16 | 479 | — | — | — | — |
| 17 | 4704 | — | — | — | — |
| 18 | 5002 | — | — | — | — |
| 19 | 1600 | — | — | — | — |
| 20 | 1930 | — | — | — | — |
| 21 | 1891 | — | — | — | — |

TABLE 1-continued

| Example Number | Ki (nM) | | | | |
|---|---|---|---|---|---|
| | GR | PR | MR | AR | ER-α |
| 22 | 386 | | | | |
| 23 | 60 | 624 | >10,000 | 4258 | >10,000 |
| 24 | 306 | 2591 | 2899 | 3731 | >10,000 |
| 25 | 5272 | — | — | — | — |
| 26 | 734 | — | — | — | — |
| 27 | 71 | 318 | >10,000 | 3243 | >10,000 |
| 28 | 5272 | — | — | — | — |
| 29 | 4561 | — | — | — | — |
| 31 | 145 | 2681 | 3906 | 3521 | >10,000 |
| 32 | 136 | 536 | 3906 | 3521 | >10,000 |
| 33 | 2304 | — | — | — | — |
| 34 | 725 | — | — | — | — |
| 35 | 4561 | — | — | — | — |
| 36 | 38 | 2591 | 2899 | 3731 | >10,000 |
| 37 | 421 | — | — | — | — |
| 38 | 4712 | — | — | — | — |
| 39 | 127 | 510 | 2899 | 3731 | >10,000 |
| 40 | 252 | — | — | — | — |
| 41 | 4494 | — | — | — | — |
| 42 | 109 | 187 | 2899 | 2797 | >10,000 |
| 43 | 4494 | — | — | — | — |
| 44 | 287 | — | — | — | — |
| 46 | 1161 | — | — | — | — |
| 48 | 852 | — | — | — | — |
| 49 | 135 | 241 | 3906 | 1039 | >10,000 |
| 50 | 1627 | — | — | — | — |
| 51 | 167 | 1084 | >10,000 | >10,000 | >10,000 |
| 52 | 733 | 698 | 3105 | >10,000 | >10,000 |
| 53 | 788 | — | — | — | — |
| 54 | 227 | 2591 | 2899 | 3731 | >10,000 |
| 55 | 1685 | — | — | — | — |
| 56 | 1026 | — | — | — | — |
| 57 | 2029 | — | — | — | — |
| 58 | 4303 | — | — | — | — |
| 59 | 4595 | — | — | — | — |
| 60 | 4651 | — | — | — | — |
| 61 | 4595 | — | — | — | — |
| 62 | 4595 | — | — | — | — |
| 63 | 4595 | — | — | — | — |
| 64 | 5272 | — | — | — | — |
| 65 | 1787 | — | — | — | — |
| 66 | 757 | — | — | — | — |

Surprisingly, the compounds of this invention selectively modulate the glucocorticoid receptor in relation to the progesterone receptor, minerocorticoid receptor, androgen receptor, and estrogen receptor-alpha. Therefore these compounds are useful for the treatment of inflammatory, immune, adrenal imbalance, cognitive and behavioral diseases.

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil); and injectable organic esters such as ethyl oleate. Proper fluidity can be maintained, for example, by the use of coating materials such as lecithin, by the maintenance of the required particle size in the case of dispersions, and by the use of surfactants. Conversely, reduced particle size may maintain biological activity.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology,* Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Abbreviations

Abbreviations that have been used in the descriptions of the scheme and the examples that follow are: $BF_3 \cdot OEt_2$ for boron trifluoride diethyl etherate; DMF for N,N-dimethylformamide, DMSO for dimethylsulfoxide; and THF for tetrahydrofuran.

Synthetic Methods

The compounds and processes of the present invention will be better understood in connection with the following synthetic schemes which illustrate the methods by which the compounds of the invention can be prepared.

Syntheses of the compounds of the present invention are described in Scheme 1 and Scheme 2.

As exemplified in Scheme 1, benzaldehydes 1 can be treated with two equivalents of an aniline or other electron-rich aromatic compound in the presence of Lewis acids such as aluminum chloride to afford symmetric triarylmethanes A. Under similar condition using one equivalent of aniline or electron-rich aromatic compound at much lower reaction temperature, benzhydrols 1B could be formed. Benzhydryl alcohols B were then treated with a different aromatic nucleophile such as another aniline in the presence of Lewis acid such as aluminum trichloride to afford triarylmethanes C. Alcohols B could also be condensed with phenols using the conditions of the Mitsunobu reaction with reagents such as tributylphosphine and diethylazodicarboxylate to form phenyl ethers D. Treatment of 1B with thiophenols in the presence of protic acids such as p-toluenesulfonic acid as catalyst also afforded phenyl thioethers E. Deprotonation of B with base followed by quenching with aromatic isocyanates provided aminophenyl analogs F.

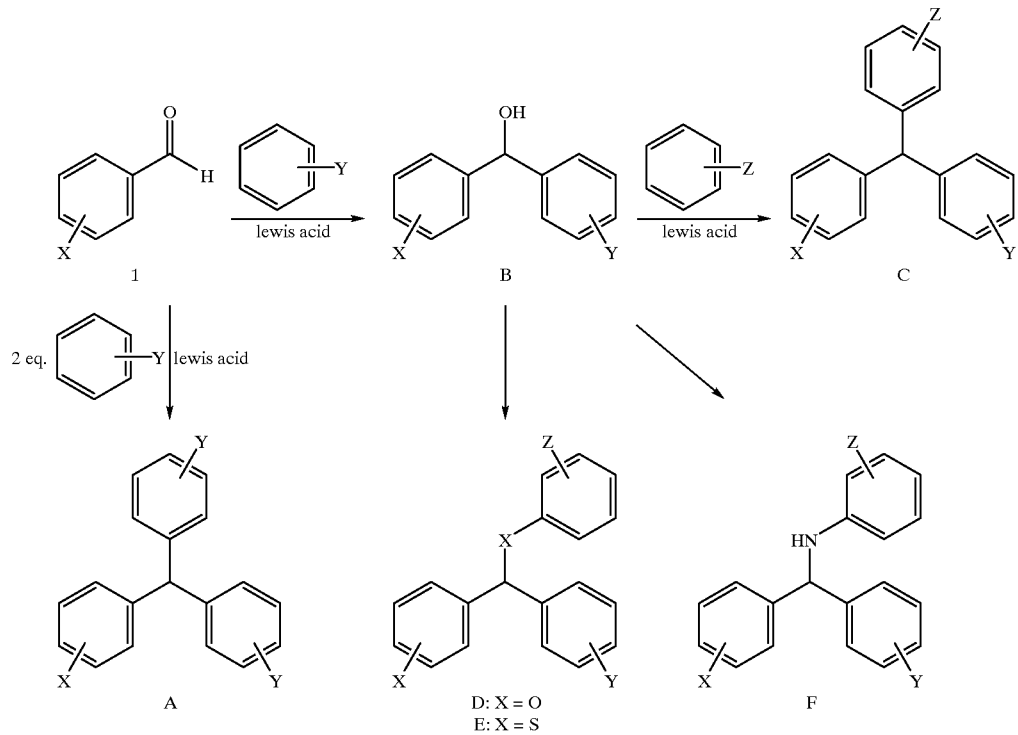

Scheme 1

Scheme 2

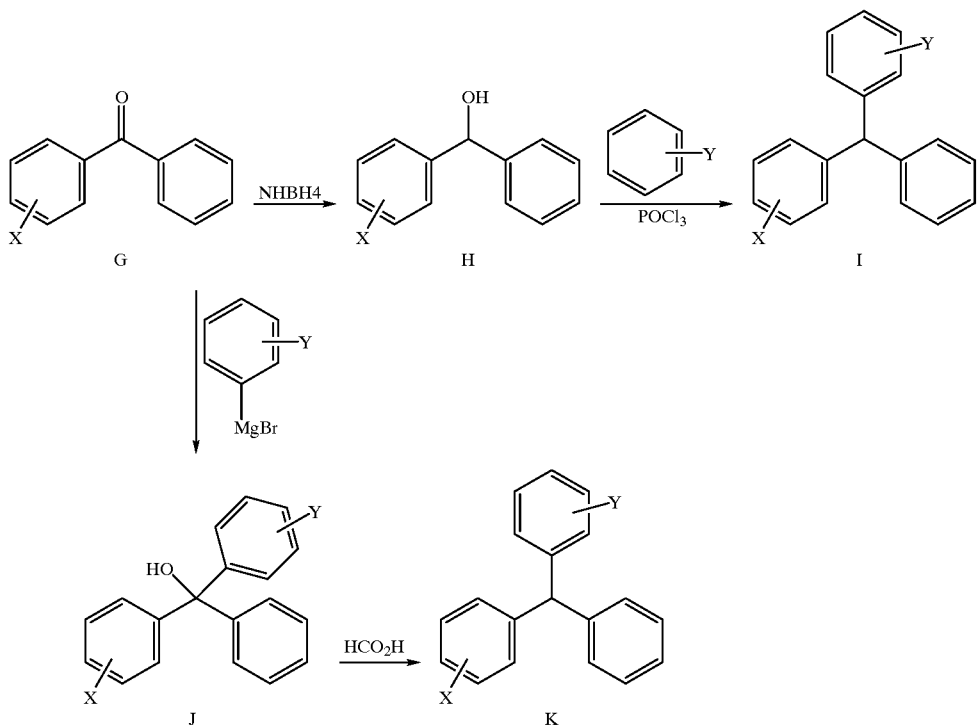

As exemplified in Scheme 2, benzophenones G can be treated with NaBH$_4$ or other reducing reagents to form benzhydrols H, which were then treated with electron-rich aromatics such as anilines in the presence of POCl$_3$ or another Lewis acid to afford triarylmethanes I. Alternatively, benzophenones G were treated with grignard reagents to form carbinols J. which were reduced with agents such as formic acid to afford triarylmethanes H.

The compounds and processes of the present invention will be better understood in connection with the following examples, which are intended as an illustration of and not a limitation upon the scope of the invention as defined in the appended claims.

EXAMPLE 1

4',4"bis(dimethylamino)-2-chloro-5-nitrotriphenylmethane

A solution of 2-chloro-5-nitrobenzaldehyde (17.28 g, 93.1 mmol) and N,N-dimethylaniline (24.78 g, 205 mmol) in CH$_2$Cl$_2$ (200 mL) at 0° C. was treated with AlCl$_3$ (13.60 g, 102 mmol) in one portion. The mixture was allowed to warm to ambient temperature overnight and quenched with aqueous 1 M NaOH. The organic phase was washed with brine and dried (Na$_2$SO$_4$), filtered, and concentrated. The crude solid was purified by trituration with 5:1 ethyl acetate/CH$_2$Cl$_2$ to provide the title compound. mp 188–190° C.;
$^1$H NMR (300 MHz, DMSO-d$_6$) δ 8.11 (dd, 1H), 7.74 (dd, 2H), 6.87 (d, 4H), 6.68 (d, 4H), 5.70 (s, 1H), 2.87 (s, 12H); MS (DCI/NH$_3$) m/e 410 (M+H)$^+$; Anal. calc'd for C$_{23}$H$_{24}$ClN$_3$O$_2$: C, 65.94; H, 6.01; N, 10.03. Found: C, 65.86; H, 5.80; N, 9.96.

EXAMPLE 2

4',4"bis(dimethylamino)-4-chloro-3-nitrotriphenylmethane

Using the procedure described for Example 1, 4-chloro-3-nitrobenzaldehyde and N,N-dimethylaniline were treated with a Lewis acid to provide the title compound.

$^1$H NMR (300 MHz, DMSO-d$_6$) δ 7.60 (d, J=2.7 Hz, 1H), 7.39 (s, J=7.8 Hz, 1H), 7.27 (dd, J=2.7, 7.8 Hz, 1H), 6.93 (d, J=9.0 Hz, 4H), 6.65 (d, J=9.0 Hz, 4H), 5.37 (s, 1H), 2.93 (s, 8H); MS (DCI/NH$_3$) m/e 410 (M+H)$^+$.

EXAMPLE 3

4',4"bis(dimethylamino)-5-acetamido-2-chlorotriphenylmethane

Using the procedure described for Example 1, 5-acetamido-2-chlorobenzaldehyde and N,N-dimethylaniline were treated with a Lewis acid to provide the title compound.

$^1$H NMR (300 MHz, DMSO-d$_6$) δ 7.75 (dd, J=2.7, 9.0 Hz, 1H), 7.28 (m, 3H), 6.95 (m, 5H), 6.63 (d, J=8.7 Hz, 4H), 5.71 (s, 1H), 2.94 (s, 12H), 2.08 (s, 3H); MS (DCI/NH$_3$) m/e 422 (M+H)$^+$; Anal. calc'd for C$_{25}$H$_{28}$ClN$_3$O: C, 71.16; H, 6.69; N, 9.96. Found: C, 71.81; H, 6.76; N, 9.96.

EXAMPLE 4

4', 4"bis(dimethylamino)-4-nitrotriphenylmethane

Using the procedure described for Example 1, 4-nitrobenzaldehyde and N,N-dimethylaniline were treated with a Lewis acid to provide the title compound. mp 181–183° C.;

$^1$H NMR (300 MHz, DMSO-d$_6$) δ 8.11 (d, J=9.0 Hz, 2H), 7.27 (d, J=9.0 Hz, 2H), 6.94 (d, J=8.7 Hz, 4H), 6.68 (d, J=8.7 Hz, 4H), 5.43 (s, 1H), 2.44 (s, 12H); MS (DCI/NH$_3$) m/e 376 (M+H)$^+$; Anal. calc'd for C$_{23}$H$_{25}$N$_3$O$_2$: C, 73.58; H,6.71 ; N, 11.19. Found: C, 73.55; H, 6.75; N, 11.16.

EXAMPLE 5

4', 4"bis(dimethylamino)-4-chlorotriphenylmethane

Using the procedure described for Example 1, 4-chlorobenzaldehyde and N,N-dimethylaniline were treated with a Lewis acid to provide the title compound. mp 98–100° C.;

$^1$H NMR (300 MHz, DMSO-d$_6$) δ 2.89 (s, 12H), 5.35 (s, 1H), 6.67 (dd, 4H), 6.94 (dd, 4H), 7.11 (dd, 2H), 7.28 (dd, 2H); MS (DCI/NH$_3$) m/e 365 (M+H)$^+$;

Anal. calc'd for C$_{23}$H$_{25}$ClN$_2$: C, 75.70; H, 6.90; N, 7.67. Found: C, 75.76; H, 6.91; N, 7.54.

EXAMPLE 6

4',4"bis(dimethylamino)-3-chlorotriphenylmethane

Using the procedure described for Example 1, 3-chlorobenzaldehyde and N,N-dimethylaniline were treated with a Lewis acid to provide the title compound. mp 102–104° C.;

$^1$H NMR (300 MHz, DMSO-d$_6$) δ 3.35 (s, 12H), 5.82 (s, 1H), 7.13 (dt, 4H), 7.40 (dt, 4H), 7.51–7.75 (m, 4H); MS (DCI/NH$_3$) m/e 365 (M+H)$^+$; Anal. calc'd for C$_{23}$H$_{25}$ClN$_2$: C, 75.70; H, 6.90; N, 7.67. Found: C, 75.76; H, 6.87; N, 7.62.

EXAMPLE 7

4',4"bis(dimethylamino)-2-chlorotriphenylmethane

Using the procedure described for Example 1, 2-chlorobenzaldehyde and N,N-dimethylaniline were treated with a Lewis acid to provide the title compound. mp 144–145° C.;

$^1$H NMR (300 MHz, DMSO-d$_6$) δ 2.90 (s, 6H), 5.74 (s, 1H), 6.67 (d, J=9 Hz, 4H), 6.89 (d, J=9 Hz, 4H), 7.03 (m, 1H), 7.22 (m, 2H), 7.37 (m, 1H); MS (DCI/NH$_3$) m/e 382 (M+NH$_4$)$^+$, 365 (M+H)$^+$; Anal. calc'd for C$_{23}$H$_{25}$ClN$_2$: C, 75.70; H, 6.90; N, 7.67. Found: C, 75.76; H, 6.81; N, 7.57.

EXAMPLE 8

4',4"bis(dimethylamino)-2-methoxytriphenylmethane

Using the procedure described for Example 1, 2-methoxybenzaldehyde and N,N-dimethylaniline were treated with a Lewis acid to provide the title compound. mp 151–153 C.;

MS (DCI/NH$_3$) m/e 361 (M+H)$^+$; Anal. calc'd for C$_{24}$H$_{28}$N$_2$O: C, 79.96; H, 7.82; N, 7.77. Found: C, 79.85; H, 7.71; N, 7.70.

EXAMPLE 9

4',4"bis(dimethylamino)-3-nitrotriphenylmethane

Using the procedure described for Example 1, 3-nitrobenzaldehyde and N,N-dimethylaniline were treated with a Lewis acid to provide the title compound. mp 141–142° C.;

$^1$H NMR (300 MHz, DMSO-d$_6$) δ 8.08 (dt, J=6.3, 2.7 Hz, 1H), 7.90 (m, 1H), 7.58 (m, 2H), 6.91 (d, J=9.0 Hz, 4H), 6.63 (d, J=9.0 Hz, 4H), 5.54 (s, 1H), 2.83 (s, 12H); MS (DCI/NH$_3$) m/e 376 (M+H)$^+$; Anal. calc'd for C$_{23}$H$_{25}$N$_3$O$_2$: C, 72.70; H, 6.76; N, 11.05. Found: C, 72.83; H, 6.62; N, 11.02.

EXAMPLE 10

4',4"bis(dimethylamino)-2-trifluoromethyltriphenylmethane

Using the procedure described for Example 1, 2-trifluoromethylbenzaldehyde and N,N-dimethylaniline were treated with a Lewis acid to provide the title compound. mp 94–96° C.; Anal. calc'd for C$_{24}$H$_{25}$F$_3$N$_2$: C, 72.34; H, 6.32; N, 7.03. Found: C, 72.12; H, 6.29; N, 7.00.

EXAMPLE 11

4', 4"bis(dimethylamino)triphenylmethane

Using the procedure described for Example 1, benzaldehyde and N,N-dimethylaniline were treated with a Lewis acid to provide the title compound. mp 100–102° C.

EXAMPLE 12

4', 4"bis(dimethylamino)-2-chloro-6-nitrotriphenylmethane

Using the procedure described for Example 1, 2-chloro-6-nitrobenzaldehyde and N,N-dimethylaniline were treated with a Lewis acid to provide the title compound.

$^1$H NMR (300 MHz, DMSO-d$_6$) δ 7.57 (dd, J=1.5, 8.4 Hz, 1H), 7.43 (dd, J=1.5, 8.4 Hz, 1H), 7.28 (t, J=8.4 Hz, 1H), 6.98 (d, J=9.0 Hz, 4H), 6.64 (d, J=9.0 Hz, 4H), 6.02 (s, 1H), 2.42 (s, 12H); MS (DCI/NH$_3$) m/e 410 (M+H)$^+$; Anal. calc'd for C$_{23}$H$_{24}$ClO$_2$N$_3$: C, 67.39; H, 5.9; N, 10.25. Found: C, 67.29; H, 5.87; N, 10.07.

EXAMPLE 13

4', 4"bis(N-piperidinyl)-2-chloro-5-nitrotriphenylmethane

Using the procedure described for Example 1, 2-chloro-5-nitrobenzaldehyde and N-phenylpiperidine were treated with a Lewis acid to provide the title compound.

$^1$H NMR (300 MHz, DMSO-d$_6$) δ 8.02 (dd, J=3.0, 9.0 Hz, 1H), 7.88 (d, J=3.0 Hz, 1H), 7.50 (d, J=9.0 Hz, 1H), 6.91 (d, J=9.0 Hz, 4H), 6.83 (d, J=9.0 Hz, 4H), 5.77 (s, 1H), 3.15 (t, J=5.4 Hz, 8H), 1.70 (m, 8H), 1.55 (m, 4H); MS (DCI/NH$_3$) m/e 490 (M+H)$^+$; Anal. calc'd for C$_{29}$H$_{32}$N$_3$ClO$_2$: C, 71.08; H, 6.56; N, 8.57. Found: C, 70.94; H, 6.48; N, 8.47.

EXAMPLE 14

4', 4"bis(dimethylamino)-2-bromotriphenylmethane

Using the procedure described for Example 1, 2-bromobenzaldehyde and N,N-dimethylaniline were treated with a Lewis acid to provide the title compound. mp 152–153° C.; Anal. calc'd for C$_{23}$H$_{25}$BrN$_2$: C, 67.48; H, 6.15; N, 6.84. Found: C, 67.28; H, 6.21; N, 6.84.

EXAMPLE 15

4',4"bis(dimethylamino)-2-methyltriphenylmethane

Using the procedure described for Example 1, o-tolualdehyde and N,N-dimethylaniline were treated with a Lewis acid to provide the title compound. mp 98–100° C.; Anal. calc'd for C$_{24}$H$_{28}$N$_2$: C, 83.67; H, 8.19; N, 8.13. Found: C, 83.72; H, 8.31; N, 8.07.

EXAMPLE 16

4', 4"bis(dimethylamino)-2,3,5-trichlorotriphenylmethane

Using the procedure described for Example 1, 2,3,5-trichlorobenzaldehyde and N,N-dimethylaniline were treated with a Lewis acid to provide the title compound. mp 149–151° C.; Anal. calc'd for C$_{23}$H$_{23}$Cl$_3$N$_2$: C, 63.68; H, 5.34; N, 6.45. Found: C, 63.39; H, 5.11; N, 6.35.

EXAMPLE 17

4', 4"bis(dimethylamino)-2-chloro-5-trifluoromethyltriphenylmethane

Using the procedure described for Example 1, 2-chloro-5-trifluoromethylbenzaldehyde and N,N-dimethylaniline were treated with a Lewis acid to provide the title compound. mp 143–145° C.; Anal. calc'd for C$_{24}$H$_{24}$ClF$_3$N$_2$: C, 66.58; H, 5.58 ; N, 6.47. Found: C, 66.40; H, 5.78; N, 6.37.

EXAMPLE 18

4', 4"bis(dimethylamino)-2,4-dichlorotriphenylmethane

Using the procedure described for Example 1, 2,4-dichlorobenzaldehyde and N,N-dimethylaniline were treated with a Lewis acid to provide the title compound. mp 104–105° C.; Anal. calc'd for C$_{23}$H$_{24}$Cl$_2$N$_2$: C, 69.17; H, 6.05; N, 7.01. Found: C, 69.17; H, 5.83; N, 6.90.

EXAMPLE 19

4',4"bis(dimethylamino)-2-chloro-4,5-methylenedioxytriphenylmethane

Using the procedure described for Example 1, 2-chloro-4,5-methylenedioxybenzaldehyde and N,N-dimethylaniline were treated with a Lewis acid to provide the title compound. mp 168–170° C.; Anal. calc'd for $C_{24}H_{25}ClN_2O_2$: C, 70.49; H, 6.16; N, 6.85. Found: C, 70.19; H, 5.99; N, 6.63.

EXAMPLE 20

4',4"bis(dimethylamino)-2,6-dichlorotriphenylmethane

Using the procedure described for Example 1, 2,6-dichlorobenzaldehyde and N,N-dimethylaniline were treated with a Lewis acid to provide the title compound. mp 134–136° C.; Anal. calc'd for $C_{23}H_{24}Cl_2N_2$: C, 69.17; H, 6.05; N, 7.01. Found: C, 68.95; H, 5.93; N, 6.81.

EXAMPLE 21

4', 4"bis(dimethylamino)-23-dichlorotriphenylmethane

Using the procedure described for Example 1, 2,3-dichlorobenzaldehyde and N,N-dimethylaniline were treated with a Lewis acid to provide the title compound. mp 172–174° C.; Anal. calc'd for $C_{23}H_{24}Cl_2N_2$: C, 69.17; H, 6.05 ; N, 7.01. Found: C, 69.08; H, 5.93; N, 6.89.

EXAMPLE 22

4',4"bis(N-morpholinyl)-2-chloro-5-nitrotriphenylmethane

Using the procedure described for Example 1, 2-chloro-5-nitrobenzaldehyde and N-phenyl morpholine were treated with a Lewis acid to provide the title compound. mp 126–128° C.;
$^1$H NMR (300 MHz, DMSO-$d_6$) δ 8.02 (dd, J=3.0, 9.0 Hz, 1H), 7.88 (d, J=3.0 Hz, 1H) 7.53 (d, J=9.0 Hz, 1H), 6.95 (d, J=8.8 Hz, 4 H), 6.83 (d, J=8.8 Hz, 4H), 3.88 (t, J=4.5 Hz, 8H), 3.15 (t, J=4.5 Hz, 8H); MS (DCI/NH$_3$) m/e 494 (M+H)$^+$; Anal. calc'd for $C_{27}H_{28}N_3O_4Cl$: C, 65.65; H, 5.71; N, 8.51. Found: C, 65.49; H, 5.65; N, 8.24.

EXAMPLE 23

4',4"bis(methylamino)-2-chloro-5-nitrotriphenylmethane

Using the procedure described for Example 1, 2-chloro-5-nitrobenzaldehyde and N-methyl aniline were treated with a Lewis acid to provide the title compound.
$^1$H NMR (300 MHz, DMSO-$d_6$) δ 8.01 (dd, J=3.0, 9.0 Hz, 1H), 8.89 (d, J=3.0 Hz, 1H), 7.53 (d, J=9.0 Hz, 1H), 6.88 (d, J=8.8 Hz, 4H), 6.55 (d, J=8.8 Hz, 4H), 5.75 (s, 1H), 3.70 (brs, 2H), 2.84 (s, 12H); MS (DCI/NH$_3$) m/e 382 (M+H)$^+$, 399 (M+NH$_4$)$^+$; Anal. calc'd for $C_{21}H_{20}N_3O_2Cl$: C, 66.05; H, 5.28; N, 1.00. Found: C, 66.01; H, 5.09; N, 10.63.

EXAMPLE 24

4',4"bis(dimethylamino)-2,5-dichlorotriphenylmethane

Using the procedure described for Example 1, 2,5-dichlorobenzaldehyde and N,N-dimethylaniline were treated with a Lewis acid to provide the title compound. mp 181–183 ° C.; Anal. calc'd for $C_{23}H_{24}Cl_2N_2$: C, 69.17; H, 6.05; N, 7.01. Found: C, 69.23; H, 6.05; N, 7.00.

EXAMPLE 25

4',4"bis(dimethylamino)-2-fluorotriphenylmethane

Using the procedure described for Example 1, 2-fluorobenzaldehyde and N,N-dimethylaniline were treated with a Lewis acid to provide the title compound. mp=129–131° C.; Anal. calc'd for $C_{23}H_{25}FN_2$: C, 79.27; H, 7.23; N, 8.03. Found: C, 79.32; H, 7.17; N, 7.96.

EXAMPLE 26

4',4"bis(dimethylamino)-2-iodotriphenylmethane

Using the procedure described for Example 1, 2-iodobenzaldehyde and N,N-dimethylaniline were treated with a Lewis acid to provide the title compound. mp 143–145° C.; Anal. calc'd for $C_{23}H_{25}IN_2$: C, 60.53; H, 5.52; N, 6.13. Found: C, 60.68; H, 5.54; N, 6.17.

EXAMPLE 27

4',4"bis(methylamino)-2,5-dichlorotriphenylmethane

Using the procedure described for Example 1, 2,5-dichlorobenzaldehyde and N-methyl aniline were treated with a Lewis acid to provide the title compound. mp 135–140° C.;
$^1$H NMR (300 MHz, DMSO-$d_6$) δ 7.48 (d, J=9.0 Hz, 1H), 7.31 (dd, J=3.0, 9.0 Hz, 1H), 6.87 (d, J=3.0 Hz, 1H), 6.76 (d, J=8.8 Hz, 4H), 6.45 (d, J=8.8 Hz, 4H), 5.58 (brs, 2H), 5.55 (s, 1H), 2.65 (s, 6H); MS (DCI/NH$_3$) m/e 371 (M+H)$^+$; Anal. calc'd for $C_{21}H_{20}N_2Cl_2$: C, 68.09; H, 5.45; N, 7.57. Found: C, 67.83; H, 5.19; N, 7.52.

EXAMPLE 28

4',4"bis(N-morpholinyl)-2,3,5-trichlorotriphenylmethane

Using the procedure described for Example 1, 2,3,5-trichlorobenzaldehyde and N-phenyl morpholine were treated with a Lewis acid to provide the title compound. mp 102–104° C.; Anal. calc'd for $C_{27}H_{27}N_2O_2Cl_3$: C, 62.78; H, 5.27; N, 5.43. Found: C, 63.19; H, 5.16; N, 4.99.

EXAMPLE 29

4',4"bis(N-pyrrolidinyl)-2-chloro-5-nitrotriphenylmethane

Using the procedure described for Example 1, 2-chloro-5-nitrobenzaldehyde and N-phenyl pyrrolidine were treated with a Lewis acid to provide the title compound. mp>200° C.; Anal. calc'd for $C_{27}H_{28}ClN_3O_2$: C, 70.19; H, 6.10; N, 9.09. Found: C, 70.45; H, 6.03; N, 8.83.

EXAMPLE 30

4',4"bis(di-n-butylamino)-2-chloro-5-nitrotriphenylmethane

Using the procedure described for Example 1, 2-chloro-5-nitrobenzaldehyde and N,N-dibutyl aniline were treated with a Lewis acid to provide the title compound. mp 69–71° C.; Anal. calc'd for $C_{35}H_{48}ClN_3O_2$: C, 72.70; H, 8.36; N, 7.26. Found: C, 73.04; H, 8.62; N, 7.32.

EXAMPLE 31

4',4"bis(N-(2-acetoxyethyl) N-methylamino)-2-chloro-5-nitrotriphenylmethane

Using the procedure described for Example 1, 2-chloro-5-nitrobenzaldehyde and N-(2-acetoxyethyl)-N-methyl aniline were treated with a Lewis acid to provide the title compound. mp 100–102° C.; Anal. calc'd for $C_{29}H_{32}ClN_3O_6$: C, 62.86; H, 5.82; N, 7.58. Found: C, 62.92; H, 5.79; N, 7.49.

EXAMPLE 32

4',4"bis(N-(2-hydroxyethyl) N-methylamino)-2-chloro-5-nitrotriphenylmethane

Using the procedure described for Example 1, 2-chloro-5-nitrobenzaldehyde and N-(2-hydroxyethyl)-N-methyl aniline were treated with a Lewis acid to provide the title compound. mp 150–152° C.; Anal. calc'd for $C_{25}H_{28}ClN_3O_4$: C, 63.89; H, 6.00; N, 8.94. Found: C, 63.72; H, 5.76; N, 8.72.

EXAMPLE 33

4',4"bis(dimethylamino)-2-chloro-5-iodotriphenylmethane

Using the procedure described for Example 1, 2-chloro-5-iodobenzaldehyde and N,N-dimethylaniline were treated with a Lewis acid to provide the title compound. Anal. calc'd for $C_{23}H_{24}N_2ClI$: C, 56.28; H, 4.93; N, 5.71. Found: C, 56.23; H, 4.79; N, 5.58.

EXAMPLE 34

4',4"bis(dimethylamino)-5-bromo-2-chlorotriphenylmethane

Using the procedure described for Example 1, 5-bromo-2-chlorobenzaldehyde and N,N-dimethylaniline were treated with a Lewis acid to provide the title compound. mp 177–178 °C.;

$^1$H NMR (300 MHz, DMSO-$d_6$) δ 7.26 (dd, J=2.7, 8.3 Hz, 1H), 7.20 (d, J=8.3 Hz, 1H), 7.12 (d, J=2.7 Hz, 1H), 6.92 (d, J=9.0 Hz, 4H), 6.67 (d, J=9.0 Hz, 4H), 5.70 (s, 1H), 3.92 (s, 12 H); MS (DCI/NH$_3$) m/e 445 (M+H)$^+$; Anal. calc'd for $C_{23}H_{24}N_2ClBr$: C, 62.25; H, 5.45; N, 6.31. Found: C, 62.06; H, 5.24; N, 6.18.

EXAMPLE 35

4',4"bis(N-(t-butoxycarbonyl) N-methylamino)-2-chloro-5-nitrotriphenylmethane

Using the procedure described for Example 1, 2-chloro-5-nitrobenzaldehyde and N-(t-butoxycarbonyl) N-methyl aniline were treated with a Lewis acid to provide the title compound. mp 180–183° C.;

$^1$H NMR (300 MHz, DMSO-$d_6$) δ 8.08 (dd, J=3.0, 8.7 Hz, 1H), 7.86 (d, J=3.0 Hz, 1H), 7.55 (d, J=8.7 Hz, 1H), 7.20 (d, J=8.7 Hz, 4H), 7.04 (d, J=8.7 Hz, 4H), 5.92 (s, 1H), 3.27 (s, 6H), 1.47 (s, 19H); MS (DCI/NH$_3$) m/e 599 (M+H)$^+$.

EXAMPLE 36

4',4"bis(N-benzylamino)-2-chloro-5-nitrotriphenylmethane

Using the procedure described for Example 1, 2-chloro-5-nitrobenzaldehyde and N-benzyl aniline were treated with a Lewis acid to provide the title compound. mp 158–160° C.;

$^1$H NMR (300 MHz, DMSO-$d_6$) δ 8.00 (dd, J=3.0, 8.8 Hz, 1H), 7.92 (d, J=3.0 Hz, 1H), 7.52 (d, J=8.8 Hz, 1H), 7.3 (m, 10H), 6.85 (d, J=9.0 Hz, 4H), 6.59 (d, J=9.0 Hz, 4H), 5.74 (s, 1H), 4.30 (s, 4H), 4.08 (brs, 2H); MS (DCI/NH$_3$) m/e 551 (M+NH$_4$)$^+$, 534 (M+H)$^+$; Anal. calc'd for $C_{33}H_{26}N_3O_2Cl$: C, 74.50; H, 4.93; N, 7.01. Found: C, 74.60; H, 4.95; N, 6.70.

EXAMPLE 37

4',4"bis(N-benzylamino)-2,5-dichlorotriphenylmethane

Using the procedure described for Example 1, 2,5-dichlorobenzaldehyde and N-benzyl aniline were treated with a Lewis acid to provide the title compound.

$^1$H NMR (300 MHz, DMSO-$d_6$) δ 7.30 (m, 1H), 7.11 (dd, J=3.0, 8.8 Hz, 1H), 6.97 (d, J=3.0 Hz, 1H), 6.85 (d, J=9.0 Hz, 4H), 6.59 (d, J=9.0 HZ, 4H), 6.59 (S, 1H), 4.30 (S, 4H), 4.02 (BRS, 2H); MS (DCI/NH$_3$) m/e 523 (M+H)$^+$; Anal. calc'd for $C_{33}H_{28}N_2Cl_2$: C, 75.71; H, 5.39; N, 5.35. Found: C, 75.41; H, 5.24; N, 5.17.

EXAMPLE 38

4',4"bis(dimethylamino)-4-methoxytriphenylmethane

Using the procedure described for Example 1, p-anisaldehyde and N,N-dimethylaniline were treated with a Lewis acid to provide the title compound. mp 101–103° C.; Anal. calc'd for $C_{24}H_{28}N_2O$: C, 79.96; H, 7.82; N, 7.77. Found: C, 79.90; H, 7.76; N, 7.74.

EXAMPLE 39

4'-dimethylamino-4"-methylamino-2-chloro-5-nitrotriphenylmethane

EXAMPLE 39A

4'-dimethylamino-2-chloro-5-nitrodiphenylmethanol

A solution of 2-chloro-5-nitrobenzaldehyde (2.09 g, 11 mmol) and N,N-dimethylaniline (1.21 g, 10 mmol) in CH$_2$Cl$_2$ (50 ml) at -78 °C was treated with solid AlCl$_3$ (1.33 portionwise. The mixture was kept at this temperature for 4 hours and quenched with aqueous 1M NaOH. The organic phase was washed with brine, dried (Na$_2$SO$_4$), filtered, and concentrated to dryness. The residue was flash chromatographed on silica gel with 10–20% ethyl acetate/hexane to provide the title compound Method C.

EXAMPLE 39B

4'-dimethylamino-4"-methylamino-2-chloro-5-nitrotriphenylmethane

A solution of Example 39A (0.31 g, 1 mmol) and N-methylaniline (0.21 g, 2 mmol) in CH$_2$Cl$_2$ (15 ml) at 0° C. was treated with solid AlCl$_3$ (0.40 g, 3 mmol) portionwise. The mixture was allowed to warm to ambient temperature overnight and quenched with aqueous 1 M NaOH. The organic phase was washed with brine, dried (Na$_2$SO$_4$), filtered, and concentrated. The residue was flash chromatographed on silica gel with 10–20% ethyl acetate/hexane to provide the title compound. mp 152–153° C.; Anal. calc'd for $C_{22}H_{22}ClN_3O_2$: C, 66.74; H, 5.60; N, 10.61. Found: C, 66.74; H, 5.70; N, 10.68.

EXAMPLE 40

4'-dimethylamino-4"-(N-morpholinyl)-2-nitrotriphenylmethane

Using the procedure described for Example 39B, a solution of Example 39A was treated with N-phenyl morpholine and a Lewis acid to provide the title compound. mp 194–196° C.; Anal. calc'd for $C_{25}H_{26}ClN_3O_3$: C, 66.43; H, 5.79; N, 9.29. Found: C, 66.52; H, 5.43; N, 9.19.

EXAMPLE 41

4'-dimethylamino-4"-(N-pyrrolidinyl)-2-chloro-5-nitrophenylmethane

Using the procedure described for Example 39B, a solution of Example 39A was treated with N-phenyl pyrrolidine and a Lewis acid to provide the title compound. mp 157–158° C.; Anal. calc'd for $C_{25}H_{26}ClN_3O_2$: C, 68.87; H, 6.01; N, 9.63. Found: C, 68.92; H, 6.02; N, 9.65.

EXAMPLE 42

4'-dimethylamino-4"-N-(2-hydroxyethyl)amino-5-nitrotriphenylmethane

Using the procedure described for Example 39B, a solution of Example 39A was treated with N-(2-hydroxyethyl)-N-methyl aniline and a Lewis acid to provide the title compound. mp 136–148° C.; Anal. calc'd for $C_{24}H_{26}ClN_3O_3$: C, 65.52; H, 5.95; N, 9.55. Found: C, 65.50; H, 5.86; N, 9.64.

EXAMPLE 43

4'-dimethylamino-4"-(di-n-butylamino)-2-chloro-5-nitrotriphenylmethane

Using the procedure described for Example 39B, a solution of Example 39A was treated with dibutylaniline and a Lewis acid to provide the title compound. mp 115–118° C.;

Anal. calc'd for $C_{29}H_{36}ClN_3O_2$: C, 70.49; H, 7.34; N, 8.50. Found: C, 70.40; H, 7.34; N, 8.58.

EXAMPLE 44

3'-methyl-4',4"-bis(dimethylamino)-2-chloro-5-nitrotriphenylmethane

Using the procedure described for Example 39B, a solution of Example 39A was treated with N,N,2-trimethylaniline and a Lewis acid to provide the title compound. mp 174–176° C.; Anal. calc'd for $C_{24}H_{26}ClN_3O_2$: C, 67.89; H, 6.18; N, 9.91. Found: C, 67.73; H, 5.82; N, 10.08.

EXAMPLE 46

4'-dimethylamino-4"-(N-piperidinyl)-2-chloro-5-nitrotriphenylmethane

Using the procedure described for Example 39B, a solution of Example 39A was treated with N-phenyl piperidine and a Lewis acid to provide the title compound. mp 166–168° C.; Anal. calc'd for $C_{26}H_{28}ClN_3O_2$: C, 69.40; H, 6.27; N, 9.33. Found: C, 69.44; H, 6.19; N, 9.20.

EXAMPLE 48

4'-methylamino-4"-(t-butoxycarbonylamino)-2-chloro-5-nitrotriphenylmethane

EXAMPLE 48A

4'-methylamino-2-chloro-5-nitrodiphenylmethanol

Using the procedure described for Example 39A, 2-chloro-5-nitrobenzaldehyde was treated with N-methyl aniline to provide the title compound.

EXAMPLE 48B

Using the procedure described for Example 39B, a solution of Example 48A was treated with N-methyl-N-(t-butoxycarbonyl) aniline and a Lewis acid to provide the title compound. mp 141–144° C.;

$^1$H NMR (300 MHz, DMSO-$d_6$) δ 8.04 (dd, J=3.0, 9.0 Hz, 1H), 7.88 (d, J=3.0 Hz, 1H), 7.55 (d, J=9.0 Hz, 1H), 7.18 (d, J=8.7 Hz, 2H), 7.02 (d, J=8.7 Hz, 2H), 6.88 (d, J=9.0 Hz, 2H), 6.54 (d, J=9.0 Hz, 2H), 5.42 (s, 1H), 3.72 (brs, 1H), 3.27 (s, 3H), 2.32 (s, 3H), 1.48 (s, 9H); MS (DCI/NH$_3$) m/e 499 (M+NH$_4$)$^+$, 481 (M+H)$^+$.

EXAMPLE 49

4'-methylamino-4"-(N-(2-acetoxyethyl)-N-methylamino)-2-chloro-5-nitrotriphenylmethane Using the procedure described for Example 39B, a solution of Example 48A was treated with N-methyl-N-(2-acetoxyethyl) aniline and a Lewis acid to provide the title compound. mp 117–119° C.; Anal. calc'd for $C_{25}H_{26}ClN_3O_4$: C, 64.16; H, 5.60; N, 8.97. Found: C, 64.22; H, 5.64; N, 8.91.

EXAMPLE 50

4'-dimethylamino-4"-(N-methyl-N-(2-benzyloxymethyl)amino)-2-chloro-5-nitrotriphenylmethane Using the procedure described for Example 60, a solution of Example 42 was treated with benzoyl chloride in dichloromethane to provide the title compound. mp 143–145° C.; Anal. calc'd for $C_{31}H_{30}ClN_3O_4$: C, 68.43; H, 5.55; N, 7.72. Found: C, 68.79; H, 5.62; N, 7.60.

EXAMPLE 51

4'-dimethylamino-4"-(N-methyl-N-(2-acetoxyethyl)amino)-2-chloro-5-nitrotriphenylmethane Using the procedure described for Example 60, a solution of Example 42 was treated with acetyl chloride in dichloromethane to provide the title compound.

EXAMPLE 52 phenyl-[(4'-dimethylaminophenyl)-(2-chloro-5-nitrophenyl)methyl]ether

A solution of Example 39A (0.31 g, 1 mmol), phenol (0.10 g, 1.1 mmol) and triphenylphosphine (0.39 g, 1.5 mmol) in THF (10 ml) at 0° C. was treated with diethylazodicarboxylate (0.27 g, 1.5 mmol). The final solution was allowed to warm to ambient temperature overnight and quenched with H$_2$O and extracted with ethyl acetate. The organic phase was washed with brine and dried (Na$_2$SO$_4$), filtered, and concentrated to dryness. The crude viscous oil was purified by flash chromatography on silica gel with 20–30% ethyl acetate/hexane to provide the title compound. mp 126–128° C.; Anal. calc'd for $C_{21}H_{19}ClN_2O_3$: C, 65.88; H, 5.00; N, 7.31. Found: C, 65.50; H, 4.89; N, 7.11.

EXAMPLE 53

4-chlorophenyl-[(4'-dimethylaminophenyl)-(2-chloro-5-nitrophenyl)methyl]ether

Using the procedure described for Example 52, a solution of Example 39A was treated with 4-chloro phenol to provide the title compound. mp 135–137° C.; Anal. calc'd for $C_{21}H_{19}Cl_2N_2O_3$: C, 60.44; H, 4.34; N, 6.71. Found: C, 60.10; H, 4.24; N, 6.56.

EXAMPLE 54 phenyl-[(4'-dimethylaminophenyl)-(2-chloro-5-nitrophenyl)methyl]thioether

A solution of Example 39A (0.31 g, 1 mmol), thiophenol (1.10 g, 10 mmol) and p-toluenesulfonic acid (19 mg, 0.1 mmol) in toluene (10 ml) was heated to reflux for 4 hours. After cooling, the solution was washed with 1M NaOH (aq) and brine respectively, dried (Na$_2$SO$_4$), filtered, and concentrated. The crude solid was purified by flash chromatography on silica gel with 10–20% ethyl acetate/hexane to provide the title compound. mp 134–136° C.; Anal. calc'd for $C_{21}H_{19}ClN_2O_2S$: C, 63.23; H, 4.80; N, 7.02. Found: C, 63.08; H, 4.54; N, 6.85.

EXAMPLE 55 phenyl-[(4'-dimethylaminophenyl)-(2-chloro-5-nitrophenyl)methyl]amine

A solution of Example 39A (0.31 g, I mmol) and phenylisocyanate (0.14 g, 1.2 mmol) in THF (10 ml) at 0° C. was treated with potassium t-butoxide (1M in THF, 0.11 ml, 1.1 mmol). The resulting solution was allowed to warm to ambient temperature overnight, quenched with H$_2$O, and extracted with ethyl acetate. The organic phase was washed with brine and dried (Na$_2$SO$_4$), filtered, and concentrated. The crude solid was purified by recrystallization from ethanol to provide the title compound. mp 195–197° C.; Anal. calc'd for $C_{21}H_{20}ClN_3O_2$: C, 65.28; H, 5.34; N, 10.87. Found: C, 65.53; H, 5.11; N, 10.79.

EXAMPLE 56

4'-dimethylamino-2-chloro-5-nitrotriphenylmethane

EXAMPLE 56A 2-chloro-5-nitrodiphenylmethanol

To a solution of 2-chloro-5-nitrobenzophenone (2.62 g, 10 mmol) in methanol (20 ml) at 0° C. was added solid NaBH$_4$ (170 mg, 4.5 mmol) in portions. The mixture was allowed to warm to ambient temperature for 4 hours, quenched with saturated NH$_4$Cl (aq) and extracted with ethyl acetate. The organic phase was washed with brine and dried (Na$_2$SO$_4$), filtered, and concentrated. The crude solid was purified by flash column chromatography with 1:5 ethyl acetate/hexanes to provide the title compound. MS (DCI/NH$_3$) m/e 264 (M+H)$^+$.

EXAMPLE 56B

4'-dimethylamino-2-chloro-5-nitrotriphenylmethane

A solution of Example 56A (0.66 g, 2.50 mmol) and POCl$_3$ in N,N-dimethylaniline (15 ml) was heated to 100° C. for 12 hours. After cooling to ambient temperature, the solution was washed with 1M NaOH (aq) and brine respectively and dried (Na$_2$SO$_4$), filtered, and concentrated. The crude solid was purified by flash column chromatography with 1:5 ethyl acetate/hexanes to provide the tide compound. mp 127–129° C.; $^1$H NMR (300 MHz, DMSO-d$_6$) δ 8.13 (dd, 1H), 7.87 (d, 1H), 7.74 (d, 1H), 7.37–7.23 (m, 3H), 7.13 (d, 2H), 6.96 (d, 2H), 6.73 (d, 2H), 5.92 (s, 1H), 2.93 (s, 6H); MS (DCI/NH$_3$) m/e 367 (M+H)$^+$; Anal. calc'd for C$_{21}$H$_{19}$ClN$_2$O$_2$: 68.75; H, 5.22; N, 7.63. Found: C, 68.87; H, 5.18; N, 7.60.

EXAMPLE 57

4'-dimethylamino-2-chlorotriphenylmethanol

A solution of N,N-dimethyl-4-bromoaniline (2.00 g, 10 mmol) and Mg (0.24 g, 10 mmol) in THF (40 ml) was heated to reflux until it became a clear solution. To this ice-cooled solution was added 2-chlorobenzophenone (2.17 g, 10 mmol) in portions. The resulting solution was allowed to warm to ambient temperature for 12 hours, quenched with saturated NH$_4$Cl (aq) and extracted with ethyl acetate. The organic phase was washed with brine and dried (Na$_2$SO$_4$), filtered, and concentrated. The crude solid was purified by flash column chromatography with 1:5 ethyl acetate/hexanes to provide the title compound. mp 130–133° C.; $^1$H NMR (300 Mhz, acetone-d$_6$) δ 7.40–7.19 (m, 8H), 7.08–7.02 (m, 3H), 6.66 (d, 2H), 2.94 (s, 6H), 2.78 (s, 1H); MS (DCI/NH$_3$) m/e 338 (M+H)$^+$; Anal. calc'd for C$_{21}$H$_{20}$ClNO: C, 74.65; H, 5.96; N, 4.14. Found: C, 74.69; H, 5.91; N, 4.15.

EXAMPLE 58

4'-dimethylamino-2-chlorotriphenylmethane

A solution of Example 57 (0.50 g, 1.48 mmol), saturated Na$_2$CO$_3$ (2 ml) and formic acid (10 ml) was heated at reflux for 12 hours. After cooling to ambient temperature, the solution was quenched with saturated Na$_2$CO$_3$ and extracted with ethyl acetate. The organic layer was washed with 1M NaOH (aq) and brine respectively and dried (Na$_2$SO$_4$), filtered, and concentrated. The residue was further treated with LiAlH$_4$ (1 M in THF, 5 ml) and quenched with saturated NH$_4$Cl (aq) followed by another extraction with ethyl acetate. The organic phase was again washed with brine and dried (Na$_2$SO$_4$), filtered, and concentrated. The crude solid was purified by flash column chromatography with 1:5 ethyl acetate/hexanes to provide the title compound. mp 122–124° C.; $^1$H NMR (300 Mhz, acetone-d6) δ 7.40–6.90 (m, 11H), 6.69(dd, 2H), 5.84 (s, 1H), 2.90 (6H); MS (DCI/NH$_3$) m/e 322 (M+H)$^+$.

EXAMPLE 59

4',4"bis(dimethylamino)-5-amino-2-chlorotriphenylmethane

A solution of Example 1 (5.0 g, 12.2 mmol) and Pd/C (5%, 0.5g) was suspended in 200 mL of methanol and degassed under vacuum. A balloon of hydrogen gas was affixed to the flask and the solution was stirred vigorously for 2 hours. The balloon was removed and the solution was again degassed and then filtered through celite. The solution was concentrated in vacuo, and the crude product was crystallized from hexane:methylene chloride (2:1) to provide the title compound. mp 194–197° C.; $^1$H NMR (300 MHz, DMSO-d$_6$) δ 6.97 (d, J=8.7 Hz, 1H), 6.88 (d, J=9 Hz, 4H), 6.65 (d, J=9.0 Hz, 4H), 6.49 (dd, J=3.0, 8.7 Hz, 1H), 6.22 (d, J=3.0 Hz, 1H), 5.50 (s, 1H), 5.10 (brs, 2H), 2.45 (s, 12H); MS (DCI/NH$_3$) m/e 380 (M+H)$^+$; Anal. calc'd for C$_{23}$H$_{26}$N$_3$Cl: C, 72.71; H, 6.90; N, 11.06. Found: C, 72.16; H, 6.87; N, 10.66.

EXAMPLE 60

4',4"bis(dimethylamino)-2-chloro-5-(4-nitrobenzamido) triphenylmethane

A solution of Example 59 (0.20 g, 0.53 mmol) in methylene chloride (5 ML) was cooled to 0° C. Diisopropylethylamine (85 mg, 0.66 mmol) was added followed by 4-nitrobenzoyl chloride (0.11 g, 0.58 mmol). The solution was stirred for 24 hours and filtered through a silica column topped with MgSO$_4$ using methylene chloride as eluent. The filtrate was concentrated in vacuo, and the crude product was crystallized from chloroform:hexane 1:3 to provide the title compound. $^1$H NMR (300 MHz, DMSO-d$_6$) δ 8.32 (d, J=8.7 Hz, 2H), 7.98 (d, J=8.7 Hz, 2H), 7.90 (d, J=8.7 Hz, 1H), 7.69 (s, 1H), 7.38 (d, J=8.7 Hz, 1H), 6.95 (d, J=9.0 Hz, 4H), 6.82 (d, J=3.0 Hz, 6.65 (d, J=9.0 Hz, 4H), 5.78 (s, 1H), 2.95 (s, 12H), ppm; Anal. calcd for C$_{30}$H$_{29}$N$_4$O$_3$Cl: C, 68.11; H, 5.53; N, 10.59. Found: C, 68.31; H, 5.45; N, 10.47.

EXAMPLE 61

4',4"bis(dimethylamino)-2-chloro-5-(4-nitrocinnamido) triphenylmethane

Using the procedure described for Example 60, a solution of Example 59 was treated with 4-nitrocinnamoyl chloride to provide the title compound. $^1$H NMR (300 MHz, DMSO-d$_6$) δ 10.39 (s, 1H), 8.29 (d, J=9.0 Hz, 2H), 7.85 (d, J=9.0 Hz, 2H), 7.81 (dd, J=3.0, 8.7 Hz, 1H), 7.68 (d, J=15.3 Hz, 1H), 7.38 (d, J=8.7 Hz, 1H), 7.23 (d, J=3.0 Hz, 1H), 6.95 (d, J=15.3 Hz, 1H), 6.88 (d, J=9.0 Hz, 4H), 6.67 (d, J=9.0 Hz, 4H), 5.62 (s, 1H), 2.85 (s, 12H); MS (DCI/NH$_3$) m/e 555 (M+H)$^+$; Anal. calc'd for C$_{32}$H$_{31}$N$_4$O$_3$Cl: C, 69.24; H, 5.63; N, 10.09. Found: C, 68.95; H, 5.45; N, 9.80.

EXAMPLE 62

4',4"bis(dimethylamino)-2-chloro-5-(cyclopropylcarbamido)-triphenylmethane

Using the procedure described for Example 60, a solution of Example 59 was treated with cyclopropanecarbonyl chloride to provide the title compound. $^1$H NMR (300 MHz, DMSO-d$_6$) δ 7.82 (d, J=8.7 Hz, 1H), 7.29 (d, J=8.7 Hz, 1H), 7.23 (s, 1H), 6.93 (d, J=9.0 Hz, 4H), 6.68 (d, J=9.0 Hz, 4H), 6.62 (s, 1H), 5.73 (s, 1H), 5.73 (s, 1H), 2.92 (s, 12H), 1.38 (m, 1H), 1.05 (m, 2H), 0.80 (m, 2H); MS (DCI/NH$_3$) m/e 448 (M+H)$^+$; Anal. calc'd for C$_{27}$H$_{30}$N$_3$ClO: C, 72.39; H, 6.75; N, 9.38. Found: C, 72.18; H, 6.66; N, 9.25.

EXAMPLE 63

4',4"bis(dimethylamino)-2-chloro-5-(dimethylsulphonimido)triphenylmethane

Using the procedure described for Example 60, a solution of Example 59 was treated with methanesulfonyl chloride to provide the title compound.

$^1$H NMR (300 MHz, DMSO-$d_6$) δ 7.43 (d, J=8.8 Hz, 1H), 7.14 (dd, J=3.0, 8.8 Hz, 1H), 6.96 (d, J=3.0 Hz, 1H), 6.93 (d, J=9.0 Hz, 4H), 6.68 (d, J=9.0 Hz, 4H), 3.25 (s, 6H), 2.93 (s, 12H); MS (DCI/NH$_3$) m/e 536 (M+H)$^+$; Anal. calc'd for $C_{25}H_{30}N_3S_2O_4Cl$: C, 56.01; H, 5.64; N, 7.84. Found: C, 55.92; H, 5.64; N, 7.73.

EXAMPLE 64

4',4"bis(dimethylamino)-2-chloro-5-(methoxycarbonylamino)triphenylmethane

Using the procedure described for Example 60, a solution of Example 59 was treated with methyl chloroformate to provide the title compound.

$^1$H NMR (300 MHz, DMSO-$d_6$) δ 7.5 (brs, 1H), 7.30 (d, J=8.8 Hz, 1H), 6.94 (d, J=9.0 Hz, 4H), 6.68 (d, J=9.0 Hz, 4H), 6.61 (dd, J=3.0, 8.8 Hz, 1H), 6.45 (s, 1H), 5.73 (s, 1H), 3.73 (s, 3H), 2.94 (s, 12H); MS (DCI/NH$_3$) m/e 438 (M+H)$^+$; Anal. calc'd for $C_{25}H_{28}N_3O_2Cl$: C, 68.62; H, 6.45; N, 9.61. Found: C, 68.96; H, 6.70; N, 9.42.

EXAMPLE 65

4',4"bis(dimethylamino)-2-chloro-5-(2-furanylmethylimino)triphenylmethane

A solution of Example 59, (0.20g, 0.53 mmol), furfural (63 mg, 0.66 mmol) and p-TsOH•H$_2$O were dissolved toluene (2 mL) and heated to 120° C. The solution was stirred at this temperature for 2 hours followed by cooling to ambient temperature. The solvent was removed in vacuo, and the crude product was crystallized from hexane:methylene chloride (2:1) to provide 0.11 g of the title compound.

$^1$H NMR (300 MHz, DMSO-$d_6$) δ 8.38 (s, 1H), 7.89 (d, J=1.0 Hz, 1H), 7.43 (d, J=8.7 Hz, 1H), 7.16 (m, 2H), 6.85 (d, J=9.0 Hz, 4H), 6.77 (d, J=3.0 Hz, 1H), 6.70 (m, 1H), 6.64 (d, J=9.0 Hz, 4H), 5.64 (s, 1H), 2.88 (s, 12H); MS (DCI/NH$_3$) m/e 458 (M+H)$^+$; Anal. calc'd for $C_{28}H_{28}N_3OCl$: C, 73.43; H, 6.16; N, 9.17. Found: C, 73.31; H, 6.12; N, 8.99.

EXAMPLE 66

4',4"bis(dimethylamino)-2-chloro-5-(2-furanylmethylimino)triphenylmethane

A solution of Example 65 (52 mg, 0.11 mmol) and sodium cyanoborohydride (7.1 mg, 0.11 mmol) were suspended in methanol (2 mL) and acetic acid (1 mL) and stirred for 12 hours. Water was added followed by extraction with methylene chloride (10 mL, 3×). The solution was dried (Na$_2$SO$_4$), filtered and reduced in vacuo. The crude product was crystallized from hexane:methylene chloride (1:1) to provide 29 mg of the title compound.

$^1$H NMR (300 MHz, DMSO-$d_6$) δ 7.33 (d, J=2.1 Hz, 1H), 7.14 (d, J=8.7 Hz, 1H), 6.39 (d, J=6.3 Hz, J=9.0 Hz, 4H), 6.68 (d, J=9.0 Hz, 4H), 6.45 (dd, J=3.0, 8.7 Hz, 1H), 6.39 (d, J=6.3 Hz, 6.36 (dd, J=2.1, 6.3 Hz, 1H), 6.08 (d, J=3.0 Hz, 1H), 5.67 (s, 1H), 4.17 (d, J=5.4 Hz, 2H), 3.92 (t, J=5.4 Hz, 1H), 2.92 (s, 12H); MS (DCI/NH$_3$) m/e 460 (M+H)$^+$.

What is claimed is:

1. A method of selectively modulating the glucocorticoid receptor-mediated gene expression in a mammal comprising administering an effective amount of a compound of Formula I

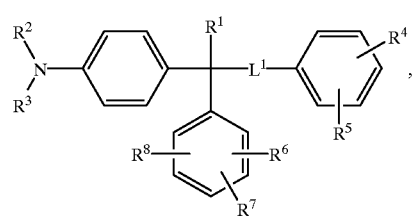

or a pharmaceutically acceptable salt or prodrug thereof, where
 $R^1$ is hydrogen;
 $L^1$ is a covalent bond;
 $R^2$ and $R^3$ are independently selected from
  (1) hydrogen, and
  (2) alkyl of one to six carbons;
 $R^4$ and $R^5$ are independently selected from
  (1) hydrogen, and
  (2) $NR^{12}R^{13}$, where $R^{12}$ and $R^{13}$ are independently selected from
   (a) hydrogen,
   (b) an amino-protecting group,
   (c) alkyl of one to six carbons, and
   (d) alkyl of one to six carbons substituted with 1, 2, or 3 substituents independently selected from
    (i) —OR$^{10}$, where R$^{10}$ is selected from
     (aa) hydrogen,
     (bb) alkyl of one to six carbons,
     (cc) a hydroxy-protecting group, and
     (dd) —C(O)R$^{11}$ where R$^{11}$ is selected from alkyl of one to six carbons, phenyl, and phenyl substituted with 1, 2, or 3 substituents independently selected from —NO$_2$, alkyl of one to six carbons, and halogen; and
    (ii) phenyl, or
  $R^{12}$ and $R^{13}$ together with the nitrogen to which they are attached for a 4 to 8 membered ring selected from the group consisting of heterocycle; and
 $R^6$, $R^7$, and $R^8$ are independently selected from
  (1) hydrogen,
  (2) halogen, and
  (3) —NO$_2$.

2. The method of claim 1 where the compound of Formula I is selected from the group consisting of
4',4"bis(dimethylamino)-2-chloro-5-nitrotriphenylmethane,
4',4"bis(methylamino)-2-chloro-5-nitrotriphenylmethane,
4',4"bis(di-n-butylamino)-2-chloro-5-nitrotriphenylmethane,
4'-dimethylamino-4"-methylamino-2-chloro-5-nitrotriphenylmethane,
4'-dimethylamino-4"(N-morpholinyl)-2-chloro-5-nitrotriphenylmethane,
4'-dimethylamino-4"-(N-pyrrolidinyl)-2-chloro-5-nitrotriphenylmethane,
4'-dimethylamino-4"-(N-methyl-N-(2-hydroxyethyl)amino)-2-chloro-5-nitrotriphenylmethane,
4'-dimethylamino-4"-(di-n-butylamino)-2-chloro-5-nitrotriphenylmethane,
3'-methyl-4',4"-bis(dimethylamino)-2-chloro-5-nitrotriphenylmethane, 4'-dimethylamino-4"-(N-piperidinyl)-2-chloro-5-nitrotriphenylmethane,
4'-methylamino-4"-(t-butoxycarbonylamino)-2-chloro-5-nitrotriphenylmethane,
4'-methylamino-4"-(N-(2-acetoxyethyl)-N-methylamino)-2-chloro-5-nitrotriphenylmethane,
4'-dimethylamino-4"-(N-methyl-N-(2-benzoyloxyethyl)amino)-2-chloro-5-nitrotriphenylmethane,
4'-dimethylamino-4"-(N-methyl-N-(2-acetoxyethyl)amino)-2-chloro-5-nitrotriphenylmethane, and
4'-dimethylamino-2-chloro-5-nitrotriphenylmethane.

3. A compound of Formula II

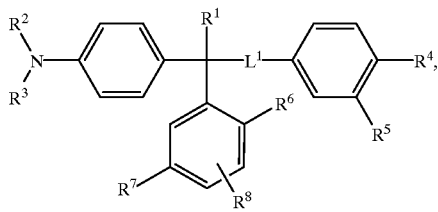

II or a pharmaceutically-acceptable salt or prodrug thereof, where $R^1$ is hydrogen;

$L^1$ is a covalent bond;

$R^2$ and $R^3$ are independently selected from
  (1) hydrogen, and
  (2) alkyl of one to six carbons;

$R^4$ and $R^5$ are independently selected from
  (1) hydrogen, and
  (2) $NR^{12}R^3$, where $R^{12}$ and $R^{13}$ are independently selected from
    (a) hydrogen,
    (b) an amino-protecting group,
    (c) alkyl of one to six carbons, and
    (d) alkyl of one to six carbons substituted with 1, 2, or 3 substituents independently selected from
      (i) —$OR^{10}$, where $R^{10}$ is selected from
        (aa) hydrogen,
        (bb) alkyl of one to six carbons,
        (cc) a hydroxy-protecting group, and
        (dd) —$C(O)R^{11}$ where $R^{11}$ is selected from alkyl of one to six carbons, phenyl, and phenyl substituted with 1, 2, or 3 substituents independently selected from —$NO_2$, alkyl of one to six carbons, and halogen; and
      (ii) phenyl, or $R^{12}$ and $R^{13}$ together with the nitrogen to which they are attached for a 4 to 8 membered ring selected from the group consisting of heterocycle; and $R^6$, $R^7$, and $R^8$ are independently selected from
  (1) hydrogen,
  (2) halogen, and
  (3) —$NO_2$.

4. A compound according to claim 3 where $R^6$ is —Cl, $R^7$ is —$NO_2$, and $R^8$ is hydrogen.

5. A compound according to claim 4 selected from the group consisting of
4',4"bis(dimethylamino)-2-chloro-5-nitrotriphenylmethane,
4',4"bis(methylamino)-2-chloro-5-nitrotriphenylmethane,
4',4"bis(di-n-butylamino)-2-chloro-5-nitrotriphenylmethane,
4'-dimethylamino-4"-methylamino-2-chloro-5-nitrotriphenylmethane,
4'-dimethylamino-4"(N-morpholinyl)-2-chloro-5-nitrotriphenylmethane,
4'-dimethylamino-4"-(N-pyrrolidinyl)-2-chloro-5-nitrotriphenylmethane, '4'-dimethylamino-4"-(N-methyl-N-(2-hydroxyethyl)amino)-2-chloro-5-nitrotriphenylmethane,
4'-dimethylamino-4"-(di-n-butylamino)-2-chloro-5-nitrotriphenylmethane,
3'-methyl-4',4"-bis(dimethylamino)-2-chloro-5-nitrotriphenylmethane,
4'-dimethylamino-4"-(N-piperidinyl)-2-chloro-5-nitrotriphenylmethane,
4'-methylamino-4"-(t-butoxycarbonylamino)-2-chloro-5-nitrotriphenylmethane,
4'-methylamino-4"-(N-(2-acetoxyethyl)-N-methylamino)-2-chloro-5-nitrotriphenylmethane,
4'-dimethylamino-4"-(N-methyl-N-(2-benzoyloxyethyl)amino)-2-chloro-5-nitrotriphenylmethane,
4'-dimethylamino-4"-(N-methyl-N-(2-acetoxyethyl)amino)-2-chloro-5-nitrotriphenylmethane, and
4'-dimethylamino-2-chloro-5-nitrotriphenylmethane.

6. A method of treating inflammation and immune, autoimmune, and inflammatory diseases in a mammal comprising administering an effective amount of a compound of Formula I.

7. A method of treating adrenal imbalance in a mammal comprising administering an effective amount of a compound of Formula I.

8. A method of treating cognitive and behavioral processes comprising administering an effective amount of a compound of Formula I.

9. A method according to claim 4 where the cognitive or behavioral process is selected from cognitive performance, memory and learning enhancement, depression, addiction, mood disorders, chronic fatigue syndrome, schizophrenia, stroke, sleep disorders, and anxiety.

* * * * *

UNITED STATES PATENT AND TRADEMARK OFFICE
CERTIFICATE OF CORRECTION

PATENT NO.    : 6,166,013
DATED         : December 26, 2000
INVENTOR(S)   : Michael J. Coghlan et al.

It is certified that error appears in the above-identified patent and that said Letters Patent is hereby corrected as shown below:

Column 1,
Line 2, replace "application Ser. No." with -- Application No. --

Column 3,
Line 24, replace "allyl" with -- alkyl --

Column 4,
Line 27, replace "$R_7$" with -- $R^7$ --

Column 8,
Line 42, replace "1 , 5" with -- 1, 5 --
Line 58, replace "undersirable" with -- undesirable --

Column 9,
Line 12, replace "The term "heterocylle" represents a represents a" with -- The term "heterocycle" represents a --

Column 11,
Line 57, replace "(~35pg protein) with -- (~35ug protein) --

Column 12,
Line 25, replace "DTf" with -- DTT --

Column 15,
Line 39, replace "on" with -- concentration --
Line 41, replace "to %" with -- to displace 50% --
Line 42, delete "inhibitory potencies of compounds of this inventionand their selectivity for GR, and ER-a receptors are shown in Table 1.
Line 43, NEW Paragraph "The inhibitory potencies of compounds of this invention and their selectivity for GR, PR, MR, AR, and ER-a receptors are shown in Table 1."

Column 23,
Line 36, replace "151-153C.;" with -- 151-153°C.; --

Column 25,
Line 50, replace "N, 1.00" with -- N, 11.00 --
Line 66, replace "mp=129-131" with -- mp 129-131--

UNITED STATES PATENT AND TRADEMARK OFFICE
CERTIFICATE OF CORRECTION

PATENT NO.   : 6,166,013
DATED        : December 26, 2000
INVENTOR(S)  : Michael J. Coghlan et al.

It is certified that error appears in the above-identified patent and that said Letters Patent is hereby corrected as shown below:

Column 27,
Line 54, replace "(m, 1H)" with -- (m, 11H) --

Column 28,
Line 10, replace "AIC1$_3$ (1.33 portionwise." with -- AlCl$_3$ (1.33g, 10 mmol) portionwise. --
Line 35, replace ")-2-nitrotriphenylmethane" with
-- )-2-chloro-5-nitrotriphenylmethane --
Line 52, replace "-4"-N-(2hydroxyethyl) amino-5-nitrotriphenylmethane with -- 4" (N-methyl-N-(2-hydroxyethyl) amino)-2-chloro-5-nitrotriphenylmethane --

Column 30,
Line 32, replace " C$_{21}$H$_{19}$C$_{12}$" with -- C$_{21}$H$_{18}$C$_{12}$ --
Line 53, replace "(0.31 g, I mmol" with -- 0.31g, 1mmol --
Line 56, replace "mol" with -- mmol --

Column 31,
Line 65, replace "acetone-d6" with -- acetone-d$_6$ --

Column 32,
Line 35, replace "d, J=8.7Hz,1H" with -- d, J=8.7Hz, 11H) --

Column 33,
Line 63, replace "6.39 (d, J=6.3Hz, J=9.0H, 4H)," with -- 6.93 (d, J=9.0Hz, 4H --

UNITED STATES PATENT AND TRADEMARK OFFICE
CERTIFICATE OF CORRECTION

PATENT NO. : 6,166,013
DATED : December 26, 2000
INVENTOR(S) : Michael J. Coghlan et al.

It is certified that error appears in the above-identified patent and that said Letters Patent is hereby corrected as shown below:

Column 35,
Line 35, replace "$NR^{12}R^3$" with -- $NR^{12}R^{13}$ --

Signed and Sealed this

Nineteenth Day of November, 2002

Attest:

JAMES E. ROGAN
Attesting Officer  Director of the United States Patent and Trademark Office